(12) United States Patent
Handa et al.

(10) Patent No.: US 12,016,974 B2
(45) Date of Patent: Jun. 25, 2024

(54) NITRIC OXIDE RELEASING SURFACES FOR DECREASED FOULING, THROMBOSIS, AND INFECTION OF MEDICAL DEVICES

(71) Applicant: University of Georgia Research Foundation, Inc., Athens, GA (US)

(72) Inventors: Hitesh Handa, Athens, GA (US); Marcus Goudie, Athens, GA (US)

(73) Assignee: UNIVERSITY OF GEORGIA RESEARCH FOUNDATION, INC., Athens, GA (US)

( * ) Notice: Subject to any disclaimer, the term of this patent is extended or adjusted under 35 U.S.C. 154(b) by 0 days.

(21) Appl. No.: 17/397,488

(22) Filed: Aug. 9, 2021

(65) Prior Publication Data

US 2021/0361834 A1 Nov. 25, 2021

Related U.S. Application Data

(62) Division of application No. 16/469,776, filed as application No. PCT/US2017/066810 on Dec. 15, 2017.

(60) Provisional application No. 62/435,706, filed on Dec. 16, 2016.

(51) Int. Cl.
| | |
|---|---|
| *A61L 29/06* | (2006.01) |
| *A61L 29/08* | (2006.01) |
| *A61L 29/16* | (2006.01) |
| *C08J 7/046* | (2020.01) |
| *C09D 183/04* | (2006.01) |

(52) U.S. Cl.
CPC ............. *A61L 29/06* (2013.01); *A61L 29/085* (2013.01); *A61L 29/16* (2013.01); *C08J 7/046* (2020.01); *C09D 183/04* (2013.01); *A61L 2300/114* (2013.01); *A61L 2420/06* (2013.01)

(58) Field of Classification Search
CPC .......................... A61L 26/0057; C09D 183/84
See application file for complete search history.

(56) References Cited

U.S. PATENT DOCUMENTS

| | | | |
|---|---|---|---|
| 6,232,434 B1 * | 5/2001 | Stamler | A61L 31/10 528/425 |
| 6,673,053 B2 * | 1/2004 | Wang | A61L 29/085 604/265 |

OTHER PUBLICATIONS

Sunenshine, Rebecca H., et al., "Multidrug-resistant Acinetobacter Infection Mortality Rate and Length of Hospitalization", Emerging Infectious Diseases, 2007, pp. 97-103, vol. 13, No. 1, www.cdc.gov/eid.

(Continued)

*Primary Examiner* — Dah-Wei D. Yuan
*Assistant Examiner* — Andrew J Bowman
(74) *Attorney, Agent, or Firm* — Thomas | Horstemeyer, LLP

(57) ABSTRACT

Embodiments of the present disclosure provide for treated articles of tubing having anti-fouling characteristics, methods of making treated articles of tubing, and the like. Disclosed herein are treated articles of tubing impregnated with a silicone oil and a nitric oxide release agent. Also described are methods for preparing a treated article of tubing and methods for delivering a pharmaceutically acceptable fluid to a subject in need thereof, wherein the fluid is transferred from a fluid source through treated articles of tubing to the subject.

8 Claims, 11 Drawing Sheets

(56) References Cited

OTHER PUBLICATIONS

Vertes, Akos, et al., "Analytical Challenges of Microbial Biofilms on Medical Devices", Analytical Chemistry, 2012, pp. 3858-3866, vol. 84, American Chemical Society, ACS Publications, doi: 10.1021/ac2029997.
Wo, Yaqi, et al., "Origin of Long-Term Storage Stability and Nitric Oxide Release Behavior of CarboSil Polymer Doped with S-Nitroso-N-acetyl-D-penicillamine", ACS Applied Materials and Interfaces, 2015, pp. 22218-22227, vol. 7, American Chemical Society, ACS Publications, doi: 10.1021/acsami.5b07501.
Wong, Tak-Sing, et al., "Bioinspired Self-Repairing Slippery Surfaces with Pressure-Stable Omniphobicity", Nature, 2011, pp. 443-447, vol. 477, doi: 10.1038/nature10447.
Worley, Brittany V., et al., "Nitric Oxide-Releasing Quaternary Ammonium-Modified Poly(amidoamine) Dendrimers as Dual Action Antibacterial Agents", Bioconjugate Chemistry, 2014, pp. 918-927, vol. 25, American Chemical Society, ACS Publications, doi: 10.1021/bc5000719.
Zheng, Sunxiang, et al., "Novel antifouling surface with improved hemocompatibility byimmobilization of polyzwitterions onto silicon via click chemistry", Applied Surface Science, 2016, pp. 619-626, vol. 363, Elsevier B.V., doi: 10.1016/j.apsusc.2015.12.081.
Ziche, M., et al., "Nitric Oxide Promotes DNA Synthesis and Cyclic GMP Formation in Endomthelial Cells From Postcapillary Venules", Biochemical and Biophysical Research Communications, 1993, pp. 1198-1203, vol. 192, No. 2, Academic Press, Inc., 006-291X/93.
Ziche, M., et al., "Nitric Oxide Promotes Proliferation and Plasminogen Activator Production by Coronary Venular Endothelium Through Endogenous bFGF", Circulation Research, 1997, pp. 1-23, vol. 80, doi: 10.1161/01.RES.80.6.845.
Annich, G. M., "Extracorporeal life support: the precarious balance of hemostasis", Journal of Thrombosis, 2015, pp. S336-S342, vol. 3, suppl. 1, International Society on Thrombosis and Haemostasis, doi: 10.1111/jth.12963.
Bondurant, Stuart, et al., editors, "Safety of Silicone Breast Implants", Committee on the Safety of Silicone Breast Implants: Division of Health Promotion and Disease Prevention-Institute of Medicine, 1999, pp. i-540, National Academy of Sciences, National Academy Press, United States of America, ISBN 0-309-06532-1 (hardcover), http://www.nap.edu/catalog/9602.html.
Brisbois, Elizabeth J., et al., "Optimized polymeric film-based nitric oxide delivery inhibits bacterial growth in a mouse burn wound model", Acta Biomaterialia, 2014, pp. 4136-4142, vol. 10, No. 10, Acta Materialia Inc., Elsevier Ltd., NIH Public Access, doi: 10.1016/j.actbio.2014.06.032.
Brisbois, Elizabeth J., et al., "Reduction in Thrombosis and Bacterial Adhesion with 7 Day Implantation of S-Nitroso-N-acetylpenicillamine (SNAP)-Doped Elast-eon E2As Catheters in Sheep", Journal of Materials Chemistry B. Materials for Biology and Medicine, 2015, pp. 1639-1645, vol. 3, No. 8, doi: doi:10.1039/C4TB02036G.
Brisbois, Elizabeth J., et al., "Long-Term Nitric Oxide Release and Elevated Temperature Stability with S-Nitroso-N-acetylpenicillamine (SNAP)-Doped Elast-eon E2As Polymer", Biomaterials, 2013, pp. 6957-6966, vol. 34, No. 28, Elsevier Ltd., NIH Public Access, doi: 10.1016/j.biomaterials.2013.05.063.
Brisbois, Elizabeth J., et al., "Recent Advances in Hemocompatible Polymers for Biomedical Applications", SpringerLink, 2014, pp. 1-68, Springer Nature Switzerland A.G., doi: 10.1007/978-3-319-12478-0_16.
Brisbois, Elizabeth J., et al., "Improved Hemocompatibility of Silicone Rubber Extracorporeal Tubing via Solvent Swelling-Impregnation of S-Nitroso-N-acetylpenicillamine (SNAP) and Evaluation in Rabbit Thrombogenicity Model", Acta Biomaterialia, 2016, pp. 111-119, vol. 37, HHS Public Access, doi: 10.1016/j.actbio.2016.04.025.
Brisbois, Elizabeth J., et al., "Attenuation of Thrombosis and Bacterial Infection using Dual Function Nitric Oxide Releasing Central Venous Catheters in a 9 day Rabbit Model", Acta Biomaterialia, 2016, pp. 304-312, vol. 44, HHS Public Access, doi: 10.1016/j.actbio.2016.08.009.
Charville, Gregory W., et al., "Reduced bacterial adhesion to fibrinogen-coated substrates via nitric oxide release", Biomaterials, 2008, pp. 4039-4044, vol. 29, No. 30, NIH Public Access, doi: 10.1016/j.biomaterials.2008.07.005.
Chen, Ya-Mei, et al., "Effectiveness of silver-impregnated central venous catheters for preventing catheter-related blood stream infections: a meta-analysis", International Journal of Infectious Diseases, 2014, pp. 279-286, vol. 29, Elsevier Ltd., doi: 10.1016/j.ijid.2014.09.018.
Chipinda, Itai and Reuben H. Simoyi, "Formation and Stability of a Nitric Oxide Donor: S-Nitroso-N-acetylpenicillamine", The Journal of Physical Chemistry B, 2006, pp. 5052-5061, vol. 110, American Chemical Society, doi: 10.1021/jp0531107.
Colletta, Alessandro, et al., "S-Nitroso-N-acetylpenicillamine (SNAP) Impregnated Silicone Foley Catheters: A Potential Biomaterial/Device To Prevent Catheter-Associated Urinary Tract Infections", ACS Biomaterials Science and Engineering, 2015, pp. 416-424, vol. 1, American Chemistry Society, ACS Publications, doi: 10.1021/acsbiomaterials.5b00032.
Coneski, Peter N., et al., "Degradable Nitric Oxide-Releasing Biomaterials via Post-Polymerization Functionalization of Cross-Linked Polyesters", Biomacromolecules, 2010, pp. 3208-3215, vol. 11, No. 11, American Chemical Society, doi: 10.1021/bm1006823.
Costerton, J. William, et al., "Microbial Biofilms", Annual Review of Microbiology, 1995, pp. 711-745, vol. 49, Annual Reviews Inc., www.annualreviews.org.
Cronin, Robert E. and Robert F. Reilly, "Unfractionated Heparin for Hemodialysis: Still the Best Option", Seminars in Dialysis, 2010, pp. 510-515, vol. 23, No. 5, Wiley Periodicals, Inc., doi: 10.1111/j.1525-139X.2010.00770.x.
De Groote, Mary Ann and Ferric C. Fang, "NO Inhibitions: Antimicrobial Properties of Nitric Oxide", Clinical Infectious Diseases, 1995, pp. S162-S165, vol. 21, suppl. 2, The University of Chicago, Oxford University Press, https://www.jstor.org/stable/4459007.
Dicks, Andrew P., et al., "Identification of Cu+ as the effective reagent in nitric oxide formation from S-nitrosothiols (RSNO)", Journal of the Chemical Society, Perkin Transactions 2, 1996, pp. 481-487, doi: 10.1039/P29960000481.
Dijkshoorn, Lenie, et al., "An increasing threat in hospitals: multidrug-resistant Acinetobacter baumannii", Nature Reviews Microbiology, 2008, pp. 939-951, vol. 5, Nature Publishing Group, www.nature.com/reviews/micro.
Fang, Ferric C., "Perspectives Series: Host/Pathogen Interactions", The Journal of Clinical Investigation, 1997, pp. 2818-2825, vol. 99, No. 12, The American Society for Clinical Investigation, Inc., doi: 0021-9738/97/06/2818/08.
Feelisch, Martin, "The use of nitric oxide donors in pharmacological studies", Naunyn-Schmiedeberg's Archives of Pharmacology, 1998, pp. 113-122, vol. 358, Springer-Verlag.
Frost, Megan C. and Mark E. Meyerhoff, "Controlled Photoinitiated Release of Nitric Oxide from Polymer Films Containing S-Nitroso-N-acetyl-DL-penicillamine Derivatized Fumed Silica Filler", Journal of American Chemical Society, 2004, pp. 1348-1349, vol. 126, American Chemical Society, doi: 10.1021/ja039466i.
Gierke, Genevieve E., et al., "S-Nitroso-N-acetyl-D-penicillamine covalently linked to polydimethylsiloxane (SNAP-PDMS) for use as a controlled photoinitiated nitric oxide release polymer", Science and Technology of Advanced Materials, 2011, pp. 1-5, vol. 12, National Institute for Materials Science, IOP Publishing, Printed in the United Kingdom, doi: 10.1088/1468-6996/12/5/055007.
Goudie, Marcus J., et al., "Characterization and in vivo performance of nitric oxide-releasing extracorporeal circuits in a feline model of thrombogenicity", Journal of Biomedical Materials Research Part A, 2017, pp. 539-546, vol. 105A, No. 2, Society for Biomaterials, Wiley Periodicals, Inc., doi: 10.1002/jbm.a.35932.
Goudie, Marcus J., et al., "Characterization of an S-nitroso-Nacetylpenicillamine-based nitric oxide releasing polymer from a translational perspective", International Journal of Polymeric Mate-

(56) References Cited

OTHER PUBLICATIONS rials and Polymeric Biomaterials, 2016, pp. 769-778, vol. 65, No. 15, Taylor & Francis Group, ISSN: 0091-4037 (Print), doi: 10.1080/00914037.2016.1163570.

Hartmann, Robert C., "Studies on the Initiation of Blood Coagulation. III. the Clotting Properties of Canine Plateletfree Plasma", Journal of Clinical Investigation, 1952, pp. 685-691, vol. 31, No. 7, doi: 10.1172/JCI102650.

Hetrick, Evan M. and Mark H. Schoenfisch, "Antibacterial nitric oxide-releasing xerogels: Cell viability and parallel plate flow cell adhesion studies", Biomaterials, 2007, pp. 1948-1956, vol. 28, Elsevier Ltd., doi: 10.1016/j.biomaterials.2007.01.006.

Jones, Mitchell Lawrence, et al., "Antimicrobial properties of nitric oxide and its application in antimicrobial formulations and medical devices", Applied Microbiology and Biotechnology, 2010, pp. 401-407, vol. 88, Springer-Verlag, doi: 10.1007/s00253-010-2733-x.

Joslin, Jessica M., et al., "Nitric Oxide Releasing Tygon Materials: Studies in Donor Leaching and Localized Nitric Oxide Release at a Polymer-Buffer Interface", ACS Applied Materials and Interfaces, 2013, pp. 9285-9294, vol. 5, American Chemical Society, ACS Publications, doi: dx.doi.org/10.1021/am402112y.

Kovach, Kyle M., et al., "The effects of PEG-based surface modification of PDMS microchannels on long-term hemocompatibility", Journal of Biomedical Materials Research Part A, 2014, pp. 4195-4205, Society for Biomaterials, Wiley Periodicals, Inc., doi: 10.1002/jbm.a.35090.

Kovach, K. M., et al., "In vitro evaluation and in vivo demonstration of a biomimetic, hemocompatible, microfluidic artificial lung", Lab on a Chip, 2015, pp. 1366-1375, vol. 15, The Royal Society of Chemistry, doi: 10.1039/c4lc01284d.

Lantvit, Sarah M., et al., "Nitric oxide releasing material adsorbs more fibrinogen", Journal of Biomedical Materials Research Part A, 2013, pp. 3201-3210, vol. 101A, No. 11, Society for Biomaterials, Wiley Periodicals, Inc., doi: 10.1002/jbm.a.34627.

Leslie, Daniel C., et al., "A Bioinspired Omniphobic Surface Coating on Medical Devices Prevents Thrombosis and Biofouling", Nature Biotechnology, 2014, pp. 1134-1140, vol. 32, No. 11, doi:10.1038/nbt.3020.

MacCullum, Noah, et al., "Liquid-Infused Silicone As a Biofouling-Free Medical Material", ACS Biomaterials Science and Engineering, 2015, pp. 43-51, vol. 1, American Chemical Society, ACS Publications, doi: 10.1021/ab5000578.

Manna, Uttam, et al., "Slippery Liquid-Infused Porous Surfaces that Prevent Microbial Surface Fouling and Kill Non-Adherent Pathogens in Surrounding Media: A Controlled Release Approach", Advanced Functional Materials, 2016, pp. 3599-3611, vol. 26, WILEY-VCH Verlag Gmbh & Co. KGaA, doi: 10.1002/adfm. 201505522.

O'Grady, Naomi P., et al., "Guidelines for the Prevention of Intravascular Catheter-Related Infections", Clinical Infectious Diseases, 2002, pp. 1281-1307, vol. 35, doi: 1058-4838/2002/3511-0001.

Paden, Matthew L., et al., "Extracorporeal Life Support Organization Registry Report 2012", ASAIO Journal, 2013, pp. 202-210, American Society for Artificial Internal Organs, doi: 10.1097/MAT.0b013e3182904a52.

Pant, Jitendra, et al., "A Multi-defense Strategy: Enhancing Bactericidal Activity of a Medical Grade Polymer with a Nitric Oxide Donor and Surface-immobilized Quaternary Ammonium Compound", Acta Biomaterialia, 2017, pp. 1-31, vol. 58, HHS Public Access, doi: 10.1016/j.actbio.2017.05.061.

Pant, Jitendra, et al., "Tunable Nitric Oxide Release from S-Nitroso-N-acetylpenicillamine via Catalytic Copper Nanoparticles for Biomedical Applications" ACS Applied Materials and Interfaces, 2017, pp. 15254-15264, vol. 9, American Chemical Society, ACS Publications, doi: 10.1021/acsami.7b01408.

Peppas, Nicholas A. and Robert Langer, "New Challenges in Biomaterials", Science, New Series, 1994, pp. 1715-1720, vol. 263, No. 5154, American Association for the Advancement of Science, https://www.jstor.org/stable/2883556.

Privett, Benjamin J., et al., "Synergy of Nitric Oxide and Silver Sulfadiazine against Gram-Negative, Gram-Positive, and Antibiotic-Resistant Pathogens", Molecular Pharmaceutics, 2010, pp. 2289-2296, vol. 7, No. 6, American Chemical Society, doi: 10.1021/mp100248e.

Privett, Benjamin J., et al., "Efficacy of surface-generated nitric oxide against Candida albicans adhesion and biofilm formation", Biofouling: The Journal of Bioadhesion and Biofilm Research, 2010, pp. 973-983, vol. 26, No. 8, Taylor & Francis Group, ISSN 1029-2454 online, doi: 10.1080/08927014.2010.534552.

Ren, Hang, et al., "Efficient Eradication of Mature Pseudomonas aeruginosa Biofilm via Controlled Delivery of Nitric Oxide Combined with Antimicrobial Peptide and Antibiotics", Frontiers in Microbiology, 2016, vol. 7, No. 1260, pp. 1-8, doi: 10.3389/fmicb.2016.01260.

Reynolds, Melissa M., et al., "Nitric Oxide Releasing Polyurethanes with Covalently Linked Diazeniumdiolated Secondary Amines", Biomacromolecules, 2006, pp. 987-994, vol. 7, No. 3, American Chemical Society, doi: 10.1021/bm0600280.

Riccio, Daniel A., "Photoinitiated Nitric Oxide-Releasing Tertiary S-Nitrosothiol-Modified Xerogels", ACS Applied Materials and Interfaces, 2012, pp. 796-804, vol. 4, American Chemical Society, ACS Publications, doi: 10.1021/am201443r.

Schairer, David O., et al., "Nitric oxide nanoparticles", Virulence, 2012, pp. 62-67, vol. 3, No. 1, Landes Bioscience, doi: 10.4161/viru.3.1.18816.

Shepherd, Greene, et al., "Adverse Drug Reaction Deaths Reported in United States Vital Statistics, 1999-2006", The Annals of Pharmacotherapy, 2012, pp. 169-175, vol. 46, doi: 1O.1345laph.1 p. 592.

Shishido, Silvia Mika, et al., "Thermal and photochemical nitric oxide release from S-nitrosothiols incorporated in Pluronic F127 gel: potential uses for local and controlled nitric oxide release", Biomaterials, 2003, pp. 3543-3553, vol. 24, Elsevier Science Ltd., doi: 10.1016/S0142-9612(03)00153-4.

Simon-Walker, Rachael, et al., "Glycocalyx-Inspired Nitric Oxide-Releasing Surfaces Reduce Platelet Adhesion and Activation on Titanium", ACS Biomaterials Science and Engineering, 2017, pp. 68-77, vol. 3, American Chemical Society, ACS Publications, doi: 10.1021/acsbiomaterials.6b00572.

Sivaraman, Balakrishnan and Robert A. Latour, "The Relationship between Platelet Adhesion on Surfaces and the Structure versus the Amount of Adsorbed Fibrinogen", Biomaterials, 2010, pp. 832-839, vol. 31, No. 5, NIH Public Access, doi: 10.1016/j.biomaterials.2009.10.008.

Sundaram, Jaya, et al., "Antimicrobial and Physicochemical Characterization of Biodegradable, Nitric Oxide-Releasing Nanocellulose-Chitosan Packaging Membranes", Journal of Agricultural and Food Chemistry, 2016, pp. 5260-5266, vol. 64, American Chemical Society, ACS Publications, doi: 10.1021/acs.jafc.6b01936.

\* cited by examiner

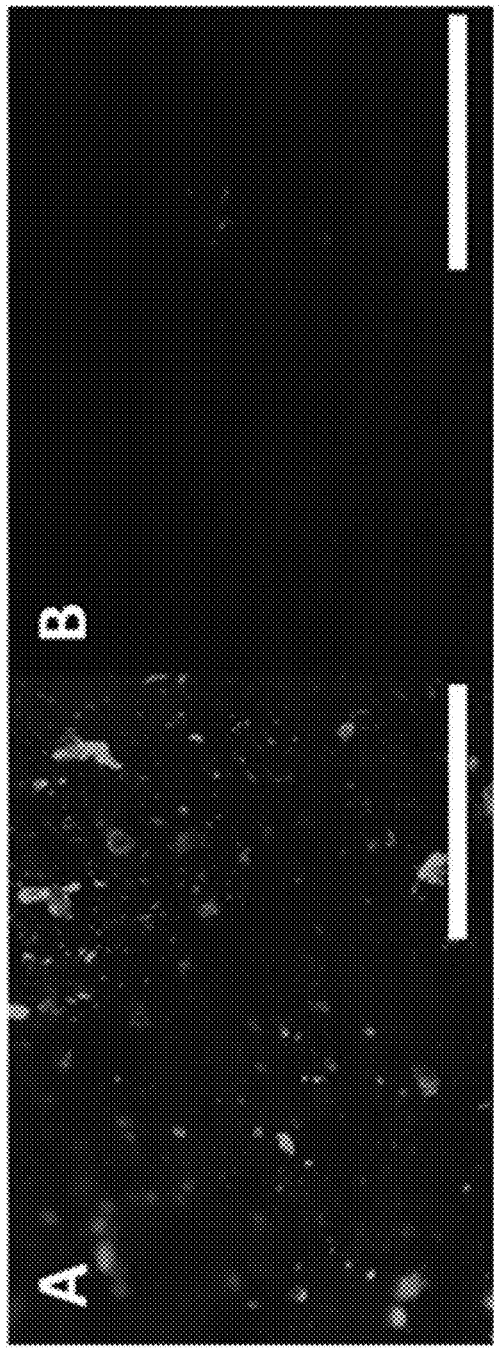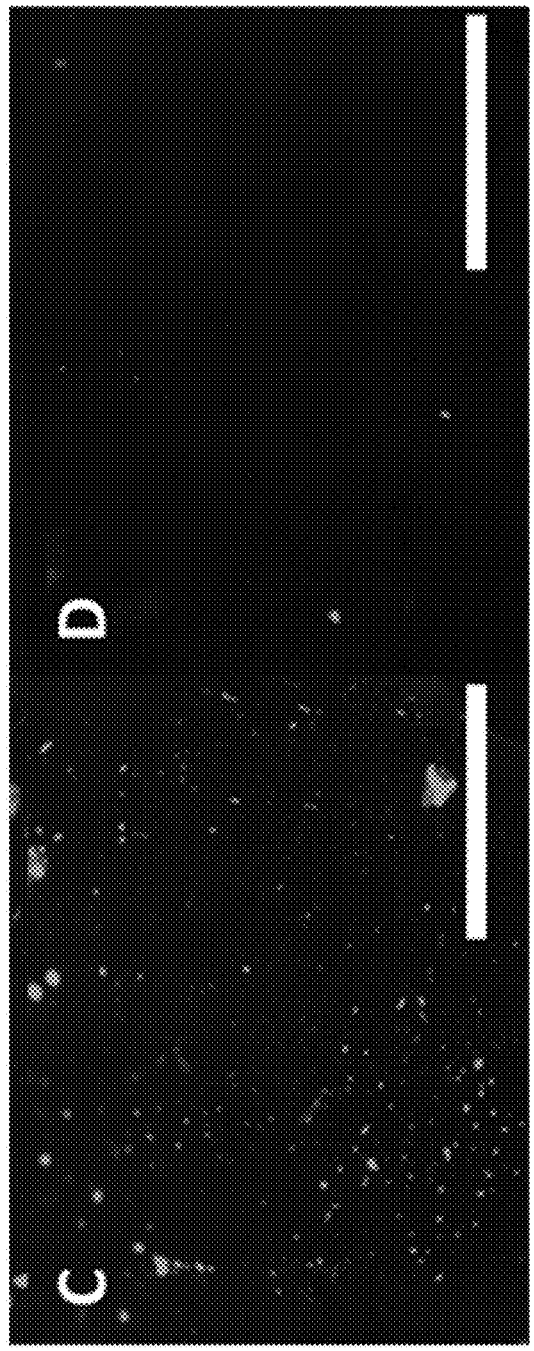
Fig. 4A  Fig. 4B  Fig. 4C  Fig. 4D

NITRIC OXIDE RELEASING SURFACES FOR DECREASED FOULING, THROMBOSIS, AND INFECTION OF MEDICAL DEVICES

CROSS-REFERENCE TO RELATED APPLICATIONS

This application is a divisional application of U.S. non-provisional application entitled "NITRIC OXIDE RELEASING SLIPPERY SURFACES FOR DECREASED FOULING, THROMBOSIS, AND INFECTION OF MEDICAL DEVICES," having Ser. No. 16/469,776 filed on Jun. 14, 2019, which is a 35 U.S.C. § 371 national stage of PCT application having serial number PCT/US2017/066810, filed on Dec. 15, 2017. This application also claims priority to U.S. provisional application entitled "NITRIC OXIDE RELEASING SLIPPERY SURFACES FOR DECREASED FOULING, THROMBOSIS, AND INFECTION OF MEDICAL DEVICES," having Ser. No. 62/435,706 filed on Dec. 16, 2016, which are entirely incorporated herein by reference.

STATEMENT REGARDING FEDERALLY SPONSORED RESEARCH OR DEVELOPMENT

This invention was made with Government support under contracts K25HL111213 and R01HL134899 awarded by the National Institutes of Health. The Government has certain rights in the invention.

BACKGROUND

Blood contacting devices (extracorporeal circuits, catheters, stents, grafts, etc.) are used in thousands of patients every day. Fouling of these devices, either through adsorption of protein leading to thrombus formation, or the adhesion of bacteria resulting in infection, are two of the most common complications seen clinically today. The ability to prevent fouling of these devices is critical for the functionality of the device and safety of the patient. While antibiotics and systemic anticoagulation have drastically improved the safety of procedures, researchers continue to strive for a completely biocompatible surface, where passive and active approaches have been developed.

Common approaches to limit the adsorption of proteins (i.e. fibrinogen) include modification of the material surface such as the immobilization of zwitterionic compounds or polyethylene glycol (PEG) and have been demonstrated to provide substantial decreases in fouling of materials both in vitro and in vivo for bacterial adhesion and thrombus formation. Immobilization of heparin have also been shown to decrease thrombus formation; however, none of these strategies have been shown to be 100% effective. A number of limitations remain with these materials, including the leaching of the surface-bound heparin, decreasing the anticoagulation activity over time, and thus require additional systemic heparin to ensure thrombus formation does not occur. While it is the current standard in clinical practice, the systemic administration of heparin can cause morbidity and mortality through post-operative bleeding, thrombocytopenia, and hypertriglyceridemia. In the case of extracorporeal circuits, while systemic anticoagulation is required to preserve the patency of the circuit, platelet consumption is still observed and can drop to <40% of the initial value during the first 1-2 hours of use. Due to these complications, the systemic administration of anticoagulants is the leading cause of drug-related deaths from adverse clinical events in the United States. Active materials such as antibiotic-releasing or silver-containing catheters are capable of limiting infection, but do not provide any mechanism for reducing thrombus formation. For this reason developing novel materials that possess ultra-low fouling characteristics with materials that can actively kill bacteria and prevent platelet activation and adhesion could provide a drastic advancement in materials for medical devices.

SUMMARY

Embodiments of the present disclosure provide for treated articles of tubing, methods of making treated articles of tubing, and the like.

An embodiment of the present disclosure provides for treated articles of tubing, wherein the treated article is impregnated with a silicone oil and a nitric oxide release agent.

Another embodiment of the present disclosure includes methods for preparing a treated article of tubing. The untreated tubing is contacted with nitric oxide release agent (NO) for a first period of time to form NO-treated tubing. The NO-treated tubing is contacted with a silicone oil for a second period of time to form the treated tubing. An aspect also includes the treated tubing made from this method.

Another embodiment of the present disclosure includes methods for preparing a treated article of tubing. The untreated tubing is contacted with nitric oxide release agent (NO) and a silicone oil form the treated tubing. An aspect also includes the treated tubing made from this method.

Another embodiment of the present disclosure includes methods for delivering a pharmaceutically acceptable fluid to a subject in need thereof, wherein the fluid is transferred from a fluid source through treated articles of tubing to the subject.

Other compositions, articles, methods, features, and advantages will be or become apparent to one with skill in the art upon examination of the following drawings and detailed description. It is intended that all such additional compositions, materials, articles, methods, features and advantages be included within this description, be within the scope of the present disclosure, and be protected by the accompanying claims.

BRIEF DESCRIPTION OF THE DRAWINGS

Further aspects of the present disclosure will be more readily appreciated upon review of the detailed description of its various embodiments, described below, when taken in conjunction with the accompanying drawings.

FIGS. 4A-D are fluorescent images showing assessment of protein adhesion (FITC labeled fibrinogen) after 2 hours incubation on (FIG. 4A) SR (FIG. 4B) LI-SR, (FIG. 4C) NOrel-SR, (FIG. 4D) LINORel tubings. Scale bar represents 250 μm.

DETAILED DESCRIPTION

Figure 1A:
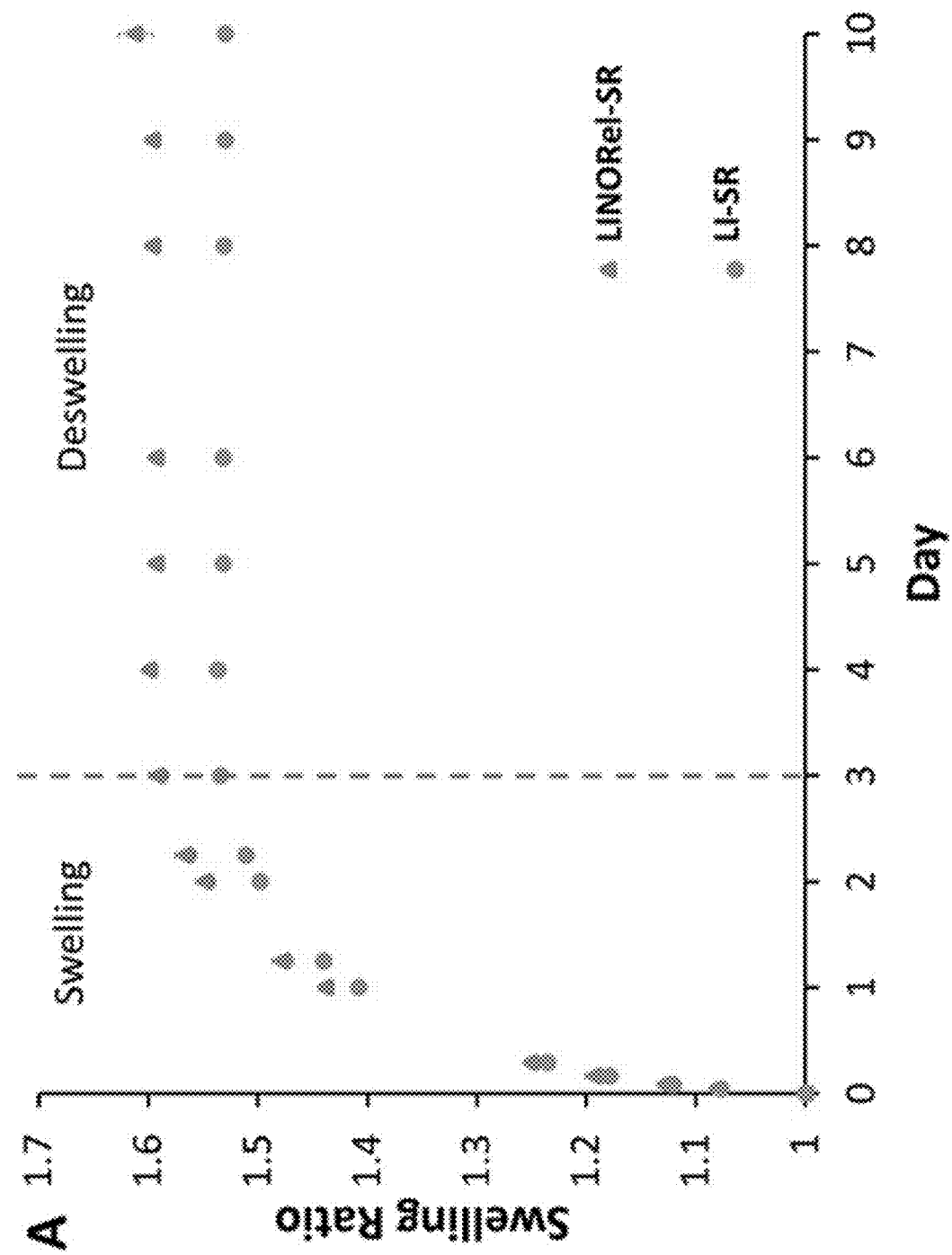
FIG. 1A plots the swelling of silicone rubber tubing with silicone oil in control and SR tubing infused with SNAP. Error bars are on the order of data point size and therefore not shown.

Before the present disclosure is described in greater detail, it is to be understood that this disclosure is not limited to particular embodiments described, and as such may, of course, vary. It is also to be understood that the terminology used herein is for the purpose of describing particular embodiments only, and is not intended to be limiting, since the scope of the present disclosure will be limited only by the appended claims.

Where a range of values is provided, it is understood that each intervening value, to the tenth of the unit of the lower limit unless the context clearly dictates otherwise, between the upper and lower limit of that range and any other stated or intervening value in that stated range, is encompassed within the disclosure. The upper and lower limits of these smaller ranges may independently be included in the smaller ranges and are also encompassed within the disclosure, subject to any specifically excluded limit in the stated range. Where the stated range includes one or both of the limits, ranges excluding either or both of those included limits are also included in the disclosure.

Unless defined otherwise, all technical and scientific terms used herein have the same meaning as commonly understood by one of ordinary skill in the art to which this disclosure belongs. Although any methods and materials similar or equivalent to those described herein can also be used in the practice or testing of the present disclosure, the preferred methods and materials are now described.

As will be apparent to those of skill in the art upon reading this disclosure, each of the individual embodiments described and illustrated herein has discrete components and features which may be readily separated from or combined with the features of any of the other several embodiments without departing from the scope or spirit of the present disclosure. Any recited method can be carried out in the order of events recited or in any other order that is logically possible.

Embodiments of the present disclosure will employ, unless otherwise indicated, techniques of chemistry, biomedicine, material science, and the like, which are within the skill of the art.

The following examples are put forth so as to provide those of ordinary skill in the art with a complete disclosure and description of how to perform the methods and use the compositions disclosed and claimed herein. Efforts have been made to ensure accuracy with respect to numbers (e.g., amounts, temperature, etc.), but some errors and deviations should be accounted for. Unless indicated otherwise, parts are parts by weight, temperature is in ° C., and pressure is at or near atmospheric. Standard temperature and pressure are defined as 20° C. and 1 atmosphere.

Before the embodiments of the present disclosure are described in detail, it is to be understood that, unless otherwise indicated, the present disclosure is not limited to particular materials, reagents, reaction materials, manufacturing processes, or the like, as such can vary. It is also to be understood that the terminology used herein is for purposes of describing particular embodiments only, and is not intended to be limiting. It is also possible in the present disclosure that steps can be executed in different sequence where this is logically possible.

It must be noted that, as used in the specification and the appended claims, the singular forms "a," "an," and "the" include plural referents unless the context clearly dictates otherwise.

Definitions

The terms "low fouling", "anti-fouling" or "anti-foul" as used herein, applies to compositions, surfaces, or articles having characteristics preventing or minimizing the adhesion of biological materials (e.g., proteins), microorganisms, or other debris.

The terms "antimicrobial" and "antimicrobial characteristic" refers to the ability to kill and/or inhibit the growth of microorganisms. A substance having an antimicrobial characteristic may be harmful to microorganisms (e.g., bacteria, fungi, protozoans, algae, and the like). A substance having an antimicrobial characteristic can kill the microorganism and/or prevent or substantially prevent the growth or reproduction of the microorganism.

The terms "bacteria" or "bacterium" include, but are not limited to, Gram positive and Gram negative bacteria. Bacteria can include, but are not limited to, *Abiotrophia, Achromobacter, Acidaminococcus, Acidovorax, Acinetobacter, Actinobacillus, Actinobaculum, Actinomadura, Actinomyces, Aerococcus, Aeromonas, Afipia, Agrobacterium, Alcaligenes, Alloiococcus, Alteromonas, Amycolata, Amycolatopsis, Anaerobospirillum, Anabaena affinis* and other *cyanobacteria* (including the *Anabaena, Anabaenopsis, Aphanizomenon, Camesiphon, Cylindrospermopsis, Gloeobacter Hapalosiphon, Lyngbya, Microcystis, Nodularia, Nostoc, Phormidium, Planktothrix, Pseudoanabaena, Schizothrix, Spirulina, Trichodesmium,* and *Umezakia* genera) *Anaerorhabdus, Arachnia, Arcanobacterium, Arcobacter, Arthrobacter, Atopobium, Aureobacterium, Bacteroides, Balneatrix, Bartonella, Bergeyella, Bifidobacterium, Bilophila* Branhamella, *Borrelia, Bordetella, Brachyspira, Brevibacillus, Brevibacterium, Brevundimonas, Brucella, Burkholderia, Buttiauxella, Butyrivibrio, Calymmatobacterium, Campylobacter, Capnocytophaga, Cardiobacterium, Catonella, Cedecea, Cellulomonas, Centipeda, Chlamydia, Chlamydophila, Chromobacterium, Chyseobacterium, Chryseomonas, Citrobacter, Clostridium, Collinsella, Comamonas, Corynebacterium, Coxiella, Cryptobacterium, Delftia, Dermabacter, Dermatophilus, Desulfomonas, Desulfovibrio, Dialister, Dichelobacter, Dolosicoccus, Dolosigranulum, Edwardsiella, Eggerthella, Ehrlichia, Eikenella, Empedobacter, Enterobacter, Enterococcus, Erwinia, Erysipelothrix, Escherichia, Eubacterium, Ewingella, Exiguobacterium, Facklamia, Filifactor, Flavimonas, Flavobacterium, Francisella, Fusobacterium, Gardnerella, Gemella, Globicatella, Gordona, Haemophilus, Hafnia, Helicobacter, Helococcus, Holdemania lgnavigranum, Johnsonella, Kin-* gella, *Klebsiella, Kocuria, Koserella, Kurthia, Kytococcus, Lactobacillus, Lactococcus, Lautropia, Leclercia, Legionella, Leminorella, Leptospira, Leptotrichia, Leuconostoc, Listeria, Listonella, Megasphaera, Methylobacterium, Microbacterium, Micrococcus, Mitsuokella, Mobiluncus, Moellerella, Moraxella, Morganella, Mycobacterium, Mycoplasma, Myroides, Neisseria, Nocardia, Nocardiopsis, Ochrobactrum, Oeskovia, Oligella, Orientia, Paenibacillus, Pantoea, Parachlamydia, Pasteurella, Pediococcus, Peptococcus, Peptostreptococcus, Photobacterium, Photorhabdus, Phytoplasma, Plesiomonas, Porphyrimonas, Prevotella, Propionibacterium, Proteus, Providencia, Pseudomonas, Pseudonocardia, Pseudoramibacter, Psychrobacter, Rahnella, Ralstonia, Rhodococcus, Rickettsia Rochalimaea Roseomonas, Rothia, Ruminococcus, Salmonella, Selenomonas, Serpulina, Serratia, Shewenella, Shigella, Simkania, Slackia, Sphingobacterium, Sphingomonas, Spirillum, Spiroplasma, Staphylococcus, Stenotrophomonas, Stomatococcus, Streptobacillus, Streptococcus, Streptomyces, Succinivibrio, Sutterella, Suttonella, Tatumella, Tissierella, Trabulsiella, Treponema, Tropheryma, Tsakamurella, Turicella, Ureaplasma, Vagococcus, Veillonella, Vibrio, Weeksella, Wolinella, Xanthomonas, Xenorhabdus, Yersinia,* and *Yokenella.* Other examples of bacterium include *Mycobacterium tuberculosis, M. bovis, M. typhimurium, M. bovis* strain BCG, BCG substrains, *M. avium, M. intracellulare, M. africanum, M. kansasii, M. marinum, M. ulcerans, M. avium* subspecies paratuberculosis, *Staphylococcus aureus, Staphylococcus epidermidis, Staphylococcus equi, Streptococcus pyogenes, Streptococcus agalactiae, Listeria monocytogenes, Listeria ivanovii, Bacillus anthracis, B. subtilis, Nocardia asteroides,* and other *Nocardia* species, *Streptococcus viridans* group, *Peptococcus* species, *Peptostreptococcus* species, *Actinomyces israelii* and other *Actinomyces* species, and *Propionibacterium acnes, Clostridium tetani, Clostridium botulinum,* other *Clostridium* species, *Pseudomonas aeruginosa,* other *Pseudomonas* species, *Campylobacter* species, *Vibrio cholera, Ehrlichia* species, *Actinobacillus pleuropneumoniae, Pasteurella haemolytica, Pasteurella multocida,* other *Pasteurella* species, *Legionella pneumophila,* other *Legionella* species, *Salmonella typhi,* other *Salmonella* species, *Shigella* species *Brucella abortus,* other *Brucella* species, *Chlamydi trachomatis, Chlamydia psittaci, Coxiella bumetti, Escherichia coli, Neiserria meningitidis, Neiserria gonorrhea, Haemophilus influenzae, Haemophilus ducreyi,* other *Hemophilus* species, *Yersinia pestis, Yersinia enterolitica,* other *Yersinia* species, *Escherichia coli, E. hirae* and other *Escherichia* species, as well as other *Enterobacteria, Brucella abortus* and other *Brucella* species, *Burkholderia cepacia, Burkholderia pseudomallei, Francisella tularensis, Bacteroides fragilis, Fudobascterium nucleatum, Provetella* species, and *Cowdria ruminantium,* or any strain or variant thereof. The Gram-positive bacteria may include, but is not limited to, Gram positive Cocci (e.g., *Streptococcus, Staphylococcus,* and *Enterococcus*). The Gram-negative bacteria may include, but is not limited to, Gram negative rods (e.g., Bacteroidaceae, Enterobacteriaceae, Vibrionaceae, Pasteurellae and Pseudomonadaceae). In an embodiment, the bacteria can include *Mycoplasma pneumoniae.*

The term "substituted" refers to any one or more hydrogens on the designated atom that can be replaced with a selection from the indicated group, provided that the designated atom's normal valence is not exceeded.

As used herein, "alkyl" or "alkyl group" refers to a branched saturated aliphatic hydrocarbon. Examples of alkyl include, but are not limited to, methyl, ethyl, vinyl, allyl, propyl, butyl, trifluoromethyl, pentafluoroethyl. In an embodiment, an alkyl group has 2 to 20 carbon atoms, 2 to 10 carbon atoms, 6 or less carbon atoms.

The term "substituted," as in "substituted alkyl", means that the substituted group may contain in place of one or more hydrogens a group such as alkyl, hydroxy, amino, halo, trifluoromethyl, cyano, —NH(alkyl), —N(alkyl)$_2$, alkoxy, alkylthio, or carboxy, and thus embraces the terms haloalkyl, alkoxy, fluorobenzyl, and the sulfur and phosphorous containing substitutions referred to below.

As used herein, the term "subject" includes humans, mammals (e.g., cats, dogs, horses, etc.), birds, and the like. Typical subjects to which embodiments of the present disclosure may be administered will be mammals, particularly primates, especially humans. For veterinary applications, a wide variety of subjects will be suitable, e.g., livestock such as cattle, sheep, goats, cows, swine, and the like; poultry such as chickens, ducks, geese, turkeys, and the like; and domesticated animals particularly pets such as dogs and cats. For diagnostic or research applications, a wide variety of mammals will be suitable subjects, including rodents (e.g., mice, rats, hamsters), rabbits, primates, and swine such as inbred pigs and the like. Additionally, for in vitro applications, such as in vitro diagnostic and research applications, body fluids and cell samples of the above subjects will be suitable for use, such as mammalian (particularly primate such as human) blood, urine, or tissue samples, or blood, urine, or tissue samples of the animals mentioned for veterinary applications. In some embodiments, a system includes a sample and a host. The term "living host" refers to the entire host or organism and not just a part excised (e.g., a liver or other organ) from the living host.

General Discussion

In accordance with the purpose(s) of the present disclosure, as embodied and broadly described herein, embodiments of the present disclosure, in some aspects, relate to methods of treating articles of tubing and articles of treated tubing. In general, the method can include treating an article of tubing sequentially or simultaneously with silicone oil and a nitric oxide release agent to form a treated article of tubing, wherein the tubing is impregnated with the silicone oil and the nitric oxide release agent. In an aspect, the treated tubing can have the characteristic of low adhesion to biomaterials (e.g., proteins) or microbes (e.g., bacteria).

Recent reports on liquid-infused materials have shown promise in creating ultra-low fouling surfaces, but are limited in their ability to prevent bacterial proliferation and prevent platelet activation in blood-contacting applications. In the present disclosure, a liquid-infused nitric oxide-releasing (LINORel) material is created by incorporating the nitric oxide (NO) donor S-nitroso-N-acetylpenicillamine (SNAP) and silicone oil in commercial medical grade silicone rubber tubing through a solvent swelling process. This combination provides several key advantages over previous NO-releasing materials, including decreased leaching of NO donor, controlled release of NO, and maintenance of ultra-low fouling property of liquid-infused materials. The LINORel tubing reduces protein adhesion as observed using fluorescence imaging, and platelet adhesion (81.7±2.5%) in vitro over a 2 hour period. The LINORel combination greatly reduces bacterial adhesion and biofilm formation of two most common pathogens responsible for hospital acquired infections: gram-positive *Staphylococcus aureus* and gram-negative *Pseudomonas aeruginosa* (99.3±1.9% and 88.5±3.3% respectively) over a 7-day period in a CDC bioreactor environment. Overall, the LINORel approach provides a synergistic combination of active and passive non-fouling approaches to increase biocompatibility and reduce infection associated with medical devices.

Nitric oxide-releasing (NORel) materials have been developed over the past 30 years after the discovery of NO as an important signaling molecule in a number of biological processes, of which include acting as a strong bactericidal and antithrombotic agent.[16-18] To mimic the physiological release of NO from the endothelium, various NO donors (such as S-nitrosothiols[18-20] and diazeniumdiolates[21-23]) have been developed and can be integrated into polymeric materials for localized delivery of NO. Multiple methods have been used to integrate S-nitrosothiols such as S-nitroso-N-acetylpenicillamine (SNAP) into various medical grade polymers, and include physical blending within the polymer[18,24], immobilization to the polymer backbone[25,26], or swelling into the polymer matrix[27,28]. However, NORel materials have been shown to have increased protein adhesion,[29] which can ultimately increase the likelihood of bacterial or platelet adhesion on the surface.[30] Despite increases in protein adhesion, NO-releasing materials have been shown to significantly reduce thrombus formation and presence of viable bacteria in vivo.[23,24,27,31] While NO possesses the ability to kill bacteria and prevent platelet activation, decreasing the degree of protein adsorption can act in a synergistic manner to aid in the prevention of thrombosis and bacterial adhesion. Therefore, the development of non-fouling NO-releasing materials can provide further improvements in the overall biocompatibility of existing materials.

Liquid-infused materials take advantage of capillary forces between the infused liquid and the polymer network, creating a low-adhesion interface between the material and the contacting fluid, such as blood. The idea of these slippery liquid-infused porous surfaces (SLIPS) stems from the lining of the gastrointestinal tract, where a mucous layer protects the tissues from colonization by bacteria.[32,33] These materials have shown drastic improvements in the biocompatibility on several common medical polymers, as well as decreasing the adhesion of bacteria to the surface. The efficacy of these SLIPs has been previously demonstrated using tethered perfluorocarbons with a liquid perfluorocarbon held on the surface using capillary forces, as well as the infusion of full medical grade tubing with a biocompatible oil.[11,33,34] It is also important to note that silicone oil has been shown to be nontoxic on the cellular and systemic levels in humans, making it a promising liquid for infusion of SLIPs materials.[35] While these materials provide a passive approach to limit protein or bacterial adhesion, even small amount of adsorbed fibrinogen can lead to platelet activation and adhesion, and ultimately the proliferation of bacteria that can lead to biofilm formation and infection. For example, the presence of thin silicone films has been reported to prevent thrombus formation for short durations[36], but are not capable preventing platelet activation and adhesion.[11] The question remains if bacteria or other microorganisms can breach the liquid barrier to the surface, leading to the formation of "beachheads" and enable colonization and biofouling.[37] To overcome bacterial adhesion, the combination of liquid-infused materials and release of a model antimicrobial agent triclosan has demonstrated a synergistic effect of the slippery surface with the active release of antimicrobial agents.[37] One drawback of these materials, however, is these materials do not address issues associated with platelet activation. Incorporating an active release of NO into these materials can aid in the prevention of platelet activation, while also acting as a bactericidal and fungicidal agent to prevent colonization and biofouling on the material surface.[38-41] The use of NO as an antibacterial agent is also attractive as antibiotic-resistant strains of bacteria have been increasingly problematic in the healthcare industry.[42,43]

In the present disclosure, fabrication of treated article of tubing (also referred to as "liquid-infused NO-releasing (LINORel) materials") is described, and the synergistic effect of incorporating the NO release with the ultra-low fouling capabilities of liquid-infused materials is demonstrated. In an aspect, a two-stage swelling process can be used to impregnate the NO donor SNAP and silicone oil into medical grade Tygon™ 3350 silicone rubber (SR) tubing. The presence of the infused silicone oil not only provides the desired traits of liquid-infused materials, but also acts in a manner to prevent the burst release kinetics typically associated with NO releasing materials.

Now having described aspects of the present disclosure in general, additional details are now provided. In an aspect the present disclosure includes a method of preparing a treated article of tubing, which includes contacting untreated tubing with a first solution (also referred to as the "swelling solution") including a nitric oxide release agent (NO) for a first period of time (e.g., about 1 hour to 48 hours) to form NO-treated tubing. In an aspect, the NO agent is absorbed, adsorbed, or otherwise is disposed within and/or on the material of the tubing. The NO-treated tubing is then contacted with a second solution including a silicone oil for a second period of time (e.g., about 1 hour to 7 days) to form the treated tubing. In an aspect, the treated article of tubing may be stored in the oil to increase stability. In an aspect, the silicon oil causes the material of the tubing to swell so that the silicon oil and the NO agent can be absorbed, adsorbed, or otherwise be disposed within and/or on the material of the tubing. In each step of contacting, the article of tubing can be exposed to each solution independently via soaking, spraying, pouring, infusing, swelling, combinations thereof, and the like.

In an aspect, the nitric oxide release agent can be in solution with a solvent e.g. Tetrahydrofuran (THF) to form a swelling solution. In an aspect, the amount can be about 5% swelling solution and about 95% silicone oil to about 95% swelling solution and 5% silicone oil, or any proportion in these ranges. In an aspect, the swelling solution can include a concentration of about 25 mg/mL to 125 mg/mL of the nitric oxide release agent in the solvent.

In an aspect, the present disclosure includes a method of preparing a treated article of tubing, which includes contacting untreated tubing with a composition including a nitric oxide release agent (e.g., which may be present in a solvent such as THF (e.g., swelling solution)) and a silicone oil for a period of time (e.g., about 1 hour to 7 days). In an aspect, the silicon oil causes the material of the tubing to swell so that the silicon oil and the NO agent can be absorbed, adsorbed, or otherwise be disposed within and/or on the material of the tubing. The article of tubing can be exposed to the composition via soaking, spraying, pouring, infusing, swelling, combinations thereof, and the like.

In an aspect, the nitric oxide release agent can be in solution with a solvent e.g. Tetrahydrofuran (THF) to form a swelling solution. In an aspect, swelling solution can be included in the composition used to treat tubing as described above. In an aspect, the composition can be about 5% swelling solution and 95% silicone oil, about 95% swelling solution and 5% silicone oil, or proportions between these ranges. In an aspect, the swelling solution can include a concentration of about 25 mg/mL to 125 mg/mL of the nitric oxide release agent in the solvent.

Embodiments of the present disclosure include treated articles of tubing, where an article of tubing is impregnated with silicone oil and a nitric oxide release agent. As used herein the term "impregnation" can include absorption, adsorption, swelling, covalent bonding, physical bonding, and the like. Advantageously, the treated article of tubing has anti-fouling characteristics and decreased leaching of NO.

In an aspect, the NO-release agent releases nitric oxide (NO). In various embodiments, the nitric oxide release agent is an S-nitroso thiol of formula O=N—S—R, where R can be an alkyl or aryl moiety. Reference to alkyl and aryl moieties includes substituted and unsubstituted alkyl and aryl moieties, respectively. In an aspect, the alkyl, substituted alkyl, aryl, or substituted aryl moiety can comprise from about 5 to about 20 carbons. In an embodiment, the nitric oxide release agent may be an amino acid moiety with a thio group. In another embodiment, the nitric oxide release agent can be an S-nitroso thiol. The S-nitroso thiol may be S-nitroso-N-acetylpenicillamine (SNAP), derivatives or salts thereof, S-Nitroso-glutathione, derivatives or salts thereof. Embodiments of the present disclosure include a treated article of tubing as above, where the NO-release agent includes an organic nitrate, a metal-NO complex, an N-nitrosamine, an S-nitrosothiol, or a combination thereof.

In various embodiments, the nitric oxide release agent comprises about 0.1 to about 20% by weight of the treated article of tubing, or about 1% to about 15%, or about 1% to about 10%, or about 1% to about 5%.

In an aspect, the silicon oil can include a liquid polymerized siloxane with organic side chains (e.g., alkyl, aryl, and the like) (e.g., polydimethylsiloxane). In an aspect, the silicone oil can have a formula such as $(-Si(R)_2-O-)_n$, wherein n is sufficiently high to produce polymers of a suitable viscosity. In an aspect, R can be an alkyl group (e.g., C1 to C6 linear or branched moiety), aryl, and the like, where each can be substituted or unsubstituted. In an aspect, the viscosity can be about 10 mPas to about 100000 mPas. In various embodiments, the silicone oils can be commercially available (e.g. polyphenyl-methylsiloxane, Wacker Silicon oil AP 150, Silicone oil AS 100, or Silicone oil DC 702).

In an aspect, the silicone oil can have a formula such as $(-Si(CH_3)_2-O-)_n$, wherein n is sufficiently high to produce polymers of a suitable viscosity. In an aspect, the viscosity can be about 10 mPas to about 100000 mPas, or about 10 to about 50000 mPas, or about 1000 to about 50000 mPas, or about 5000 to about 50000 mPas, or about 10000 to about 50000 mPas, or 20000 to about 50000 mPas, or about 10 mPas to about 10000 mPas, or about 10 mPas to about 5000 mPas, or about 100 mPas to about 1000 mPas, or about 100 mPas to about 500 mPas, or about 500 mPas to about 1000 mPas, or about 500 mPas to about 2000 mPas In an embodiment, the treated article of tubing includes from about 1% to about 80% by weight of silicone oil, or from about 1% to about 50% by weight, or from about 1% to about 30% by weight, or from about 1% to about 10% by weight, or from about 1% to 5% by weight.

The tubing, in various embodiments, can include an elastomer. The elastomer can include a base polymer (e.g. thermoplastic polymers, thermosetting poymers, silicone, polyvinyl chloride, polyurethane, polyimide, fluoropolymer, rubber, thermoplastic elastomer). Tubing, as used herein, can be any tube-shaped material, and can be formed by extrusion, heat-shrinking, or other methods. Examples of tubing include, but are not limited to, items used in medical settings such as catheters, intravenous delivery tubing, surgical tubing, drug delivery, angioplasty, neuromodulation, dilation. Tubing for on-medical applications such as food-grade tubing is also within the scope of the present disclosure.

In embodiments, the treated or untreated tubing can include those with chemical resistant properties (e.g. thermoplastic elastomers, styrene-ethylene-butylene modified block copolymer with silicone oil, thermal set rubber, siloxane polymers and amorphous silica, Polypropylene-based material with USP mineral oil, ePTFE (expanded PTFE) and platinum-cured silicone, ePTFE (expanded PTFE) and fluoroelastomer, polytetrafluoroethylene, thermoplastic polyurethanes (TPU), or thermoplastic olefin elastomers (TPO)). The tubing can be silicone-oil absorbing elastomeric tubing. The absorbing can include adsorption on a surface or within the tubing.

The tubing can be commercially available tubing (e.g. PharMed® BPT, PureFit® SBP, PureFit® SMP, PureFit® SVP, PureFit® SWP, SaniPure™ BDF™, SaniPure™ 60, Sani-Tech® LA-60, Sani-Tech® Sil-250, Sani-Tech® STHT™-C, Sani-Tech® STHT™-R, Sani-Tech® STHT™-R-HD, Sani-Tech® STHT™-WR, Sani-Tech® STHT™-W, CO, Tygon® 2275, Tygon® 2275 I.B., Tygon® 3350, Tygon® 3355L, Tygon® 3360LA, Tygon® 3370 I.B., Tygon® LFL, Tygon® Lab (R-3603), Tygon® LFL, Tygon® Food (B-44-4X), Tygon® Fuel & Lubricant (F-4040-A), Tygon® Chemical (2001), Versilic® SPX-50, Versilic® SPX-70 I.B., Silicone (platinum-cured), Silicone (peroxide-cured), BioPharm Silicone and BioPharm Plus Silicone (platinum-cured), Puri-Flex™, C-FLEX®, PharMed® BPT, PharmaPure®, GORE® STA-PURE® PCS, GORE® STA-PURE® PFL, PTFE, Norprene® (A 60 G), Norprene® Food (A 60 F), Chem-Durance® Bio, GORE® Style 400, Viton®).

In an embodiment, the treated article of tubing releases nitric oxide at a rate of from about $0.01 \times 10^{-10}$ mol/min-cm$^2$ to about $4 \times 10^{-10}$ mol/min-cm$^2$, or from about from about $0.05 \times 10^{-10}$ mol/min-cm$^2$ to about $2 \times 10^{-10}$ mol/min-cm$^2$, or from about $0.05 \times 10^{-10}$ mol/min-cm$^2$ to about $2 \times 10^{-10}$ mol/min-cm$^2$, or from about $0.05 \times 10^{-10}$ mol/min-cm$^2$ to about $2 \times 10^{-10}$ mol/min-cm$^2$, or from about $0.05 \times 10^{-10}$ mol/min-cm$^2$ to about $1 \times 10^{-10}$ mol/min-cm$^2$.

In an aspect, the treated article of tubing includes a tube comprising an inner surface and an outer surface, where the nitric oxide release agent releases nitric oxide at least from the inner surface. The treated article may include a silicone oil and the NO release agent on or near the inside surface but could also include deeper impregnation.

In an embodiment, the inner surface of the tubing composition or article may have a slipperiness as defined by a sliding angle test as described in one or more models of Eral, H. B., et al. "Contact angle hysteresis: a review of fundamentals and applications", Colloid Polym Sci (2013) 291: 247 (herein incorporated by reference). In an embodiment, the surface may be hydrophobic or superhydrophobic.

The present disclosure also includes method of delivering a pharmaceutically acceptable fluid to a subject in need thereof. The method can include transferring the fluid from a fluid source through an article of treated tubing as described above. Pharmaceutically acceptable fluids can include e.g. saline, plasma, blood, intravenous solutions, or any other pharmaceutically acceptable fluid known to those of skill in the art. The fluid source can include bags for intravenous administration of fluid, pump, bladder, and the like.

In a particular aspect, the present disclosure provides for:
(i) the treated articles of tubing that show reduced adhesion of the blood coagulation protein fibrinogen despite NO release; (ii) reduced platelet adhesion in vitro; (iii) and the increased efficacy of preventing biofilm formation of pathogens associated with hospital-acquired infection over a 7 day period. In an aspect, the method is the first of its kind to combine the advantages of liquid-infused materials with the active release of an antibacterial, antifungal, and antithrombotic agent.

EXAMPLES

Now having described the embodiments of the disclosure, in general, the examples describe some additional embodiments. While embodiments of the present disclosure are described in connection with the example and the corresponding text and figures, there is no intent to limit embodiments of the disclosure to these descriptions. On the contrary, the intent is to cover all alternatives, modifications, and equivalents included within the spirit and scope of embodiments of the present disclosure.

Example 1

Physical characterization of silicone tubing from SLIPs perspective—Commercial silicone tubing was impregnated with the NO donor SNAP using the previously described swelling method.[27] To demonstrate the incorporation of SNAP has an insignificant effect on the lubricating nature of the silicone oil, sliding angle and oil swelling/deswelling were investigated before and after SNAP incorporation.

The infusion of silicone oil into the silicone tubing leads to an expanded state of the polymer tubing, as the polymer chains extend to maximize the polymer-solvent interactions.[33]

To observe if the presence of SNAP within the silicone tubing altered the overall swelling capacity or kinetics, the swelling ratio of oil within the tubing was recorded over 72 hours. The presence of SNAP increased the overall swelling ratio, from $1.53\pm0.003$ to $1.59\pm0.009$ (FIG. 1A, p=0.012). The increase in swelling ratio maybe be attributed to unfavorable interactions between the polymer matrix and crystalline SNAP distributed throughout, leading to higher silicone oil uptake to minimize this interaction. The SR tubing was also capable of maintaining these swelling ratios over the 7 day period at 37° C. The ability for the tubing to maintain this swelling ratio shows that while the swelling ratio is lower than previously reported[33], the diffusion of the oil from the polymer matrix has decreased, which coincides with the increased time to reach maximum swelling. However, the decrease in swelling ratio may result in decreased thickness of the liquid layer, impacting the overall performance of the SLIP surface. The chemical structure of the elastomer to make the silicone tubing can dictate the overall swelling ratio and could pose the possibility of selecting certain swelling ratio kinetics for the desired application.

Figure 1B:
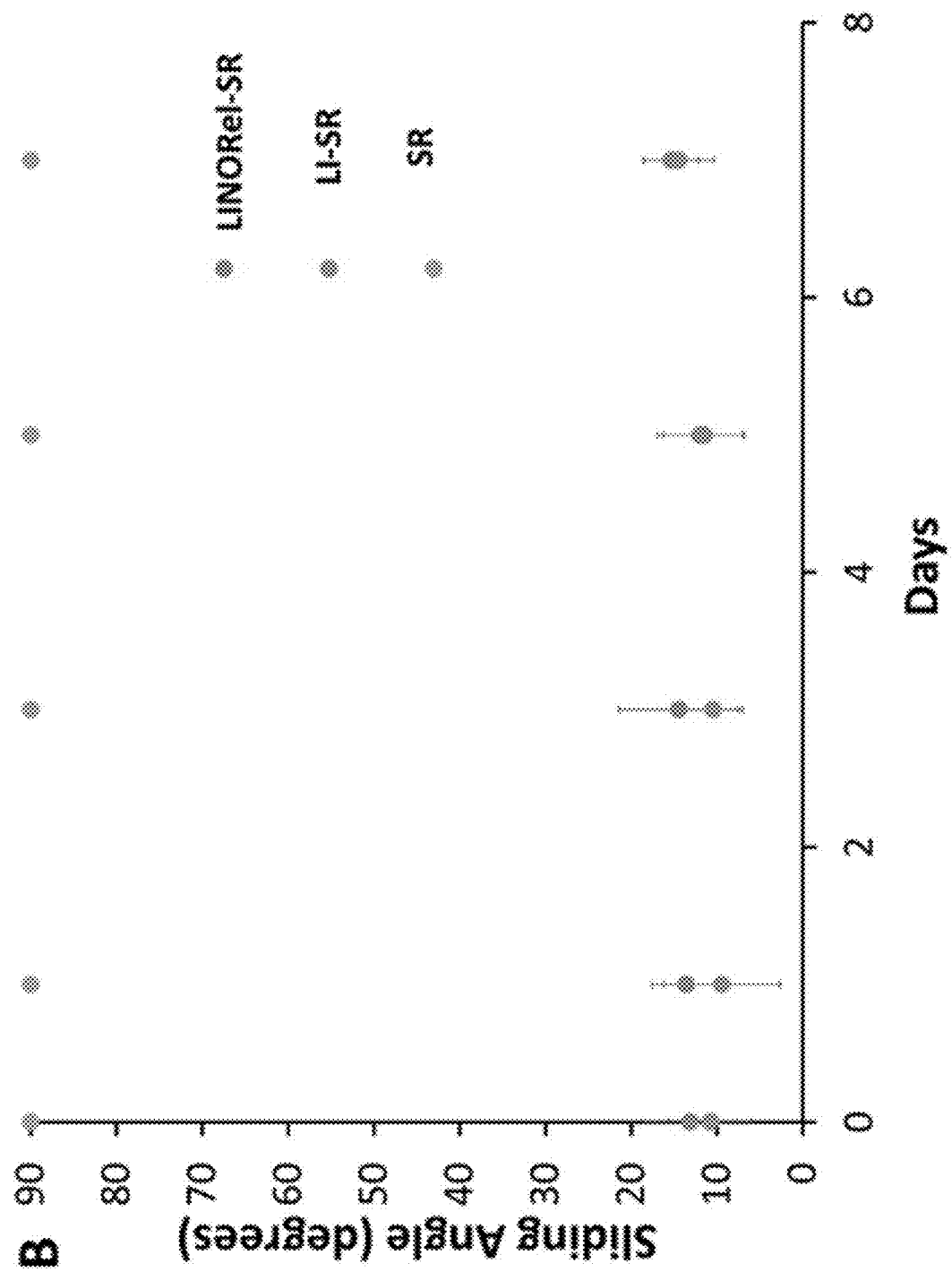
FIG. 1B shows the sliding angle of LI-SR and LINORel-SR tubing over 7 days when stored in phosphate buffered saline at 37° C.

All sliding angle measurements were taken using a 2 μL droplet, where the sample was raised slowly at one end and the angle was measured with a digital level. The liquid-infused nitric oxide-releasing (LINORel) SR tubing showed a sliding angle of $13.2\pm5.5°$, compared to oil swollen tubing which had an initial sliding angle of $10.8\pm2.4°$ (p>0.05). Both methods utilizing the incorporation of silicone oil provided drastic decreases in the observed sliding angle when compared to SR controls, which all showed sliding angles>90°. The sliding angle was observed to slightly increase over a 7 day period for both NORel-SR and LINORel-SR samples (FIG. 1B). Previous results of infused silicone report sliding angles in the single digits (2.1°).[33] However, these samples were prepared using the silicone Sylgard 184 and prepared as a flat surface. It has been shown previously that the SNAP swelling process has minimal effects on the surface morphology of the silicone tubing, and is supported by the similar sliding angles of LI-SR and LINORel-SR tubing.[27] Overall, the drastic decrease between control and the oil infused tubing are substantial in demonstrating the efficacy of the oil to increase the slippery nature of the tubing.

Characterization of Liquid-Infused NO Releasing Silicone Rubber from NO Perspective Leaching of S-nitroso-acetyl-D-penicillamine—The leaching of NO donors can have detrimental effects on the release characteristics and overall lifetime of the device. This phenomenon is generally associated with a "burst-release" of NO during the initial hours of use. Methods to limit the leaching of physically incorporated NO donors have included the use of hydrophobic polymers.[18] For NO donor-polymer combinations that have minimal leaching (<5% of the total NO donor incorporated), incubation of the device in a solution for an allotted time has been used to control the burst effect when used in vivo.[18,31] While the overall leaching of the donor is low compared to the total loading of the NO donor, the timeframe in which the donor is released to the blood stream can still have systemic effects such as vasodilation and decreases in blood pressure. Therefore, even materials that experience minimal NO donor leaching can still exhibit burst-release characteristics at implantation.

Figure 2:
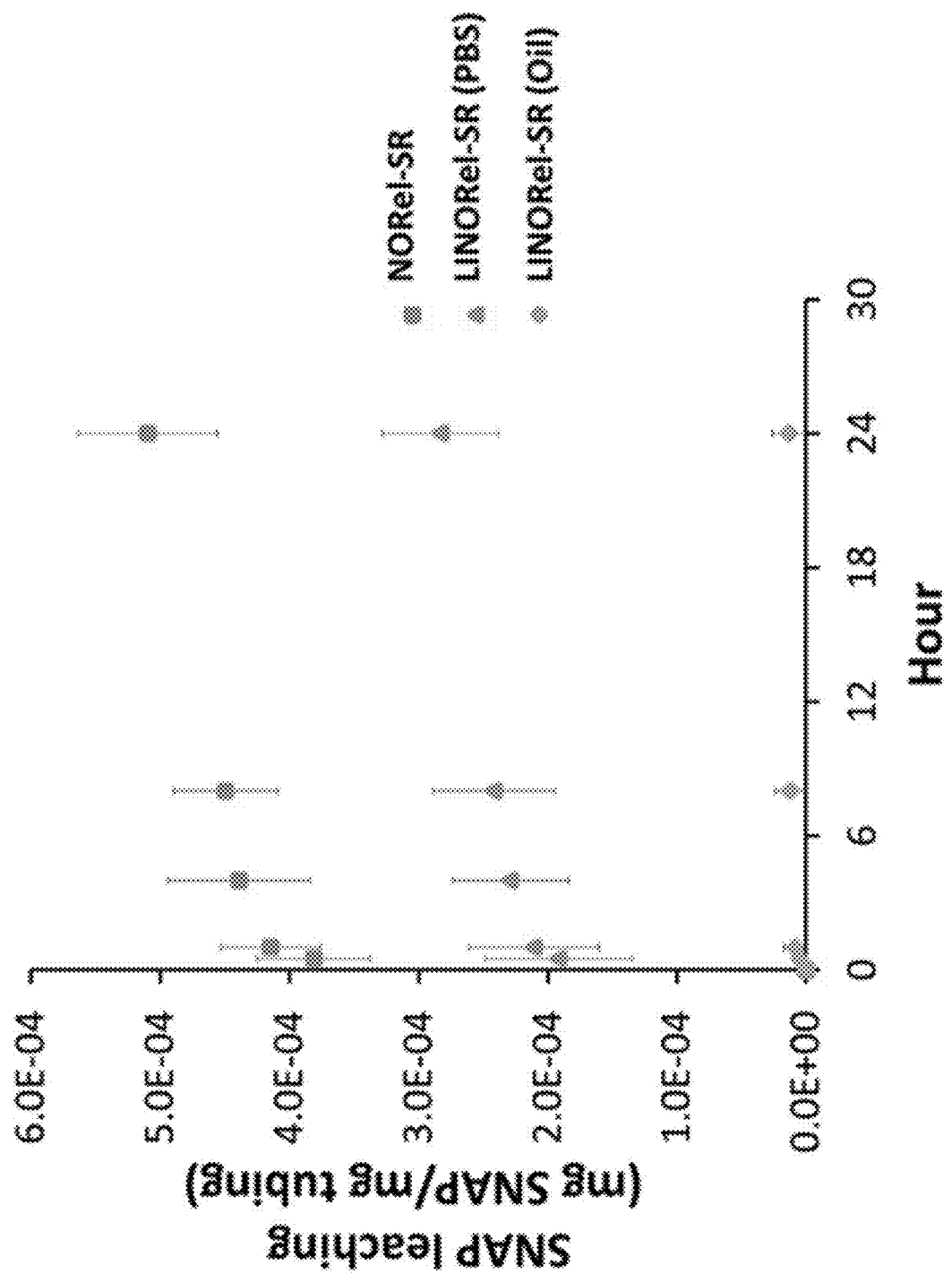
FIG. 2 shows leaching characteristics of SNAP from NORel-SR and LINORel-SR. Leaching was conducted at room temperature and samples were protected from light at all times.

The leaching of SNAP from the SR tubing was examined using UV-vis spectroscopy during both the oil swelling (72 h) as well as the first 24 hours in PBS under physiological conditions (FIG. 2). During the infusion of the tubing with silicone oil, the amount of leached SNAP was observed to not increase after the first 8 hours ($1.3\pm0.1\times10^{-5}$ mg SNAP $mg^{-1}$ tubing), which may be attributed to the solubility of SNAP (or the base molecule NAP) in the silicone oil. Solubility of SNAP in silicone oil was found to be 0.4 μg/mL. Therefore, increasing the swelling time past 8 hours should not have significant effects on the levels of SNAP within the SR tubing when compared to NORel-SR that is stored at room temperature. The stability of SNAP within a polymer matrix has been shown to retain 87% of SNAP activity after 6 months at room temperature.[44] Once placed into the aqueous environment at physiological conditions, the LINORel tubing demonstrated significantly lower leaching levels than of the NORel tubing alone over an initial 24 hour period ($5.3\pm0.4\times10^{-4}$ mg SNAP $mg^{-1}$ tubing vs. $2.9\pm1.0\times10^{-4}$ mg SNAP $mg^{-1}$ tubing, p=0.02). The total leaching of the LINORel tubing (from both oil and PBS incubation) was reduced by ca. 45% than that of NORel tubing alone.

Figure 3A:
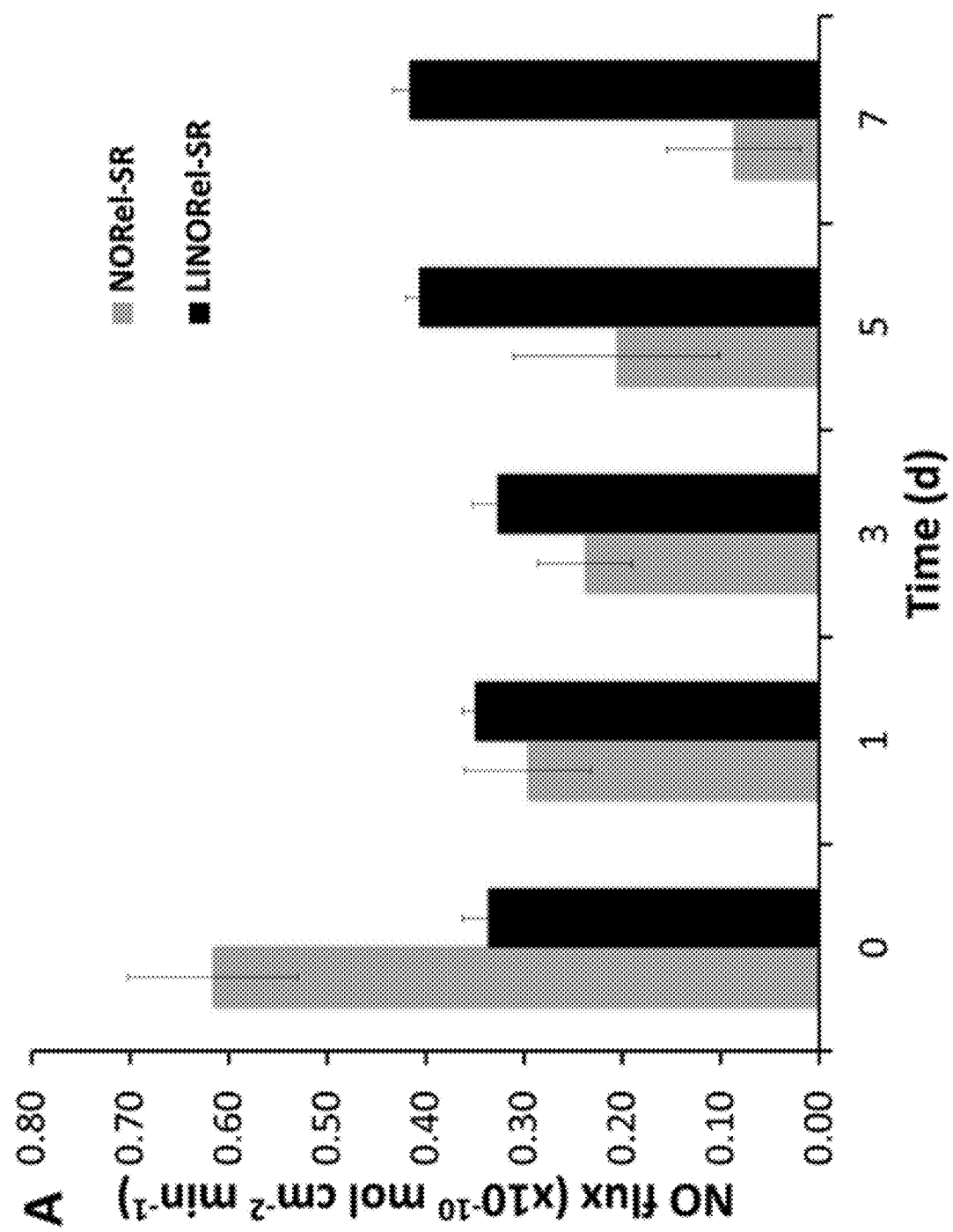
FIG. 3A shows average daily nitric oxide release measures from SNAP-SR and SNAP-Oil-SR tubing over a 7-day period. Measurements were conducted at 37° C. using a Sievers Chemiluminescence Nitric Oxide Analyzer.
Figure 3B:
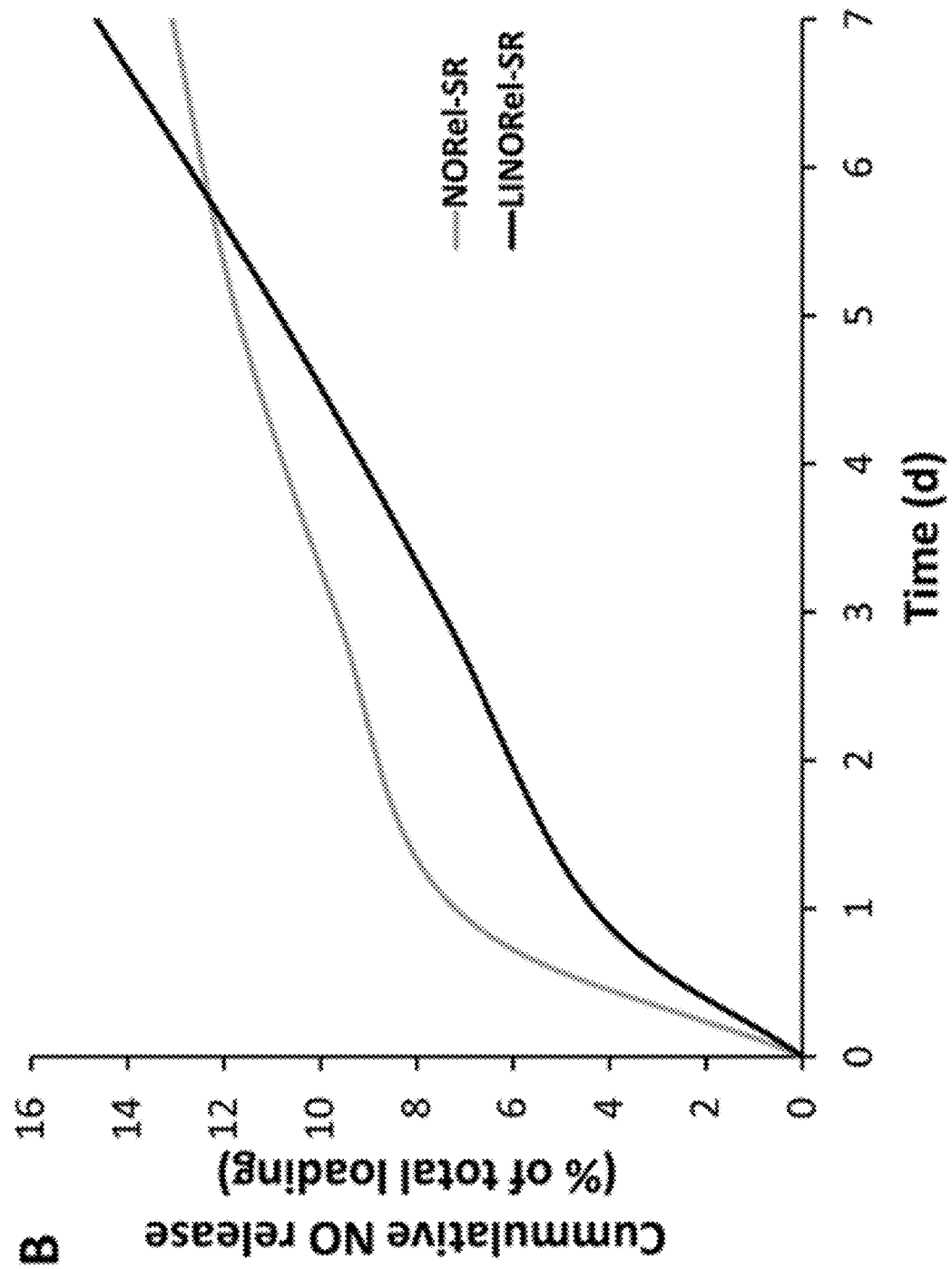
FIG. 3B shows cumulative release of NO from NORel-SR and LINORel at physiological conditions due to leaching and degradation of the NO donor.
Figure 8:
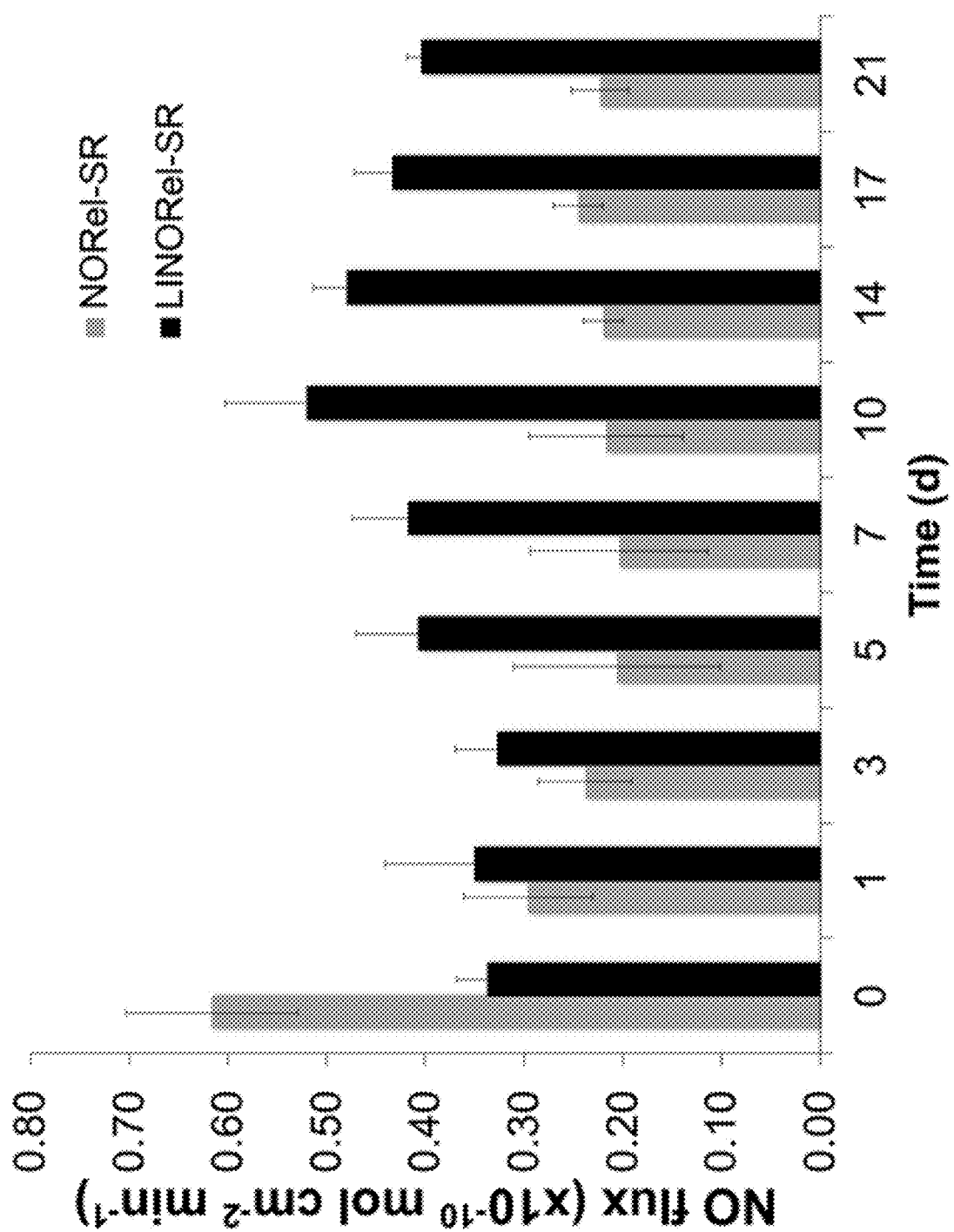
FIG. 8 illustrates extended nitric oxide release from LI-SR and LINORel-SR measured via chemiluminescence over a 21 day period.

Nitric Oxide release in vitro—Nitric oxide release was measured over a 7 day period from both NORel-SR and LINORel-SR using a Sievers chemiluminescence nitric oxide analyzer (FIG. 3A). Release of NO from the SNAP infused tubing exhibited an NO release profile that is consistent with other previously reported materials, showing higher levels of NO initially, and gradually decreasing until reaching a steady state release.[18,27,44] Controlling this burst release is a prime objective for researchers when developing new NO releasing materials, as the burst can be detrimental to the lifetime of the device. The SNAP swelling concentration of 25 mg $mL^{-1}$ was chosen as it was previously shown to provide physiological levels of NO release and significantly increase the hemocompatibility of SR tubing in vivo.[27] However, silicone Foley catheters have been shown to release NO for over 30 days when swollen with 125 mg mL$^{-1}$ SNAP in THF,[28] demonstrating that further optimization of the SNAP swelling concentration can be investigated. The total loading of SNAP using the swelling process was found to be ca. 1 wt % (via chemiluminescence) when a concentration of 25 mg mL$^{-1}$ is used, and is consitent with previous SNAP swelling reports (ca. 5 wt %, 125 mg mL$^{-1}$).[28] Release rates for the NORel-SR tubing decreased from $0.62\pm0.09\times10^{-10}$ mol min$^d$ cm$^{-2}$ to $0.09\pm0.07\times10^{-10}$ mol min$^{-1}$ cm$^{-2}$ over the 7 day period. The LINORel-SR tubing demonstrated a consistent release over the 7 day period, with initial and final release rates of $0.34\pm0.03\times10^{-10}$ mol min$^{-1}$ cm$^{-2}$ and $0.42\pm0.06\times10^{-10}$ mol min$^{-1}$ cm$^{-2}$, respectively (p>0.05). While the bactericidal activity was not examined for greater than 7 days, LINORel SR was able to provide this sustained release of NO over a 21 day period, making this a plausible approach for long term applications (FIG. 8). The cumulative release of NO from the material due to both leaching and degradation of SNAP to NAP is shown in FIG. 3B as a percentage of the total SNAP loaded. Therefore, the incorporation of the silicone oil not only assists with non-fouling capabilities of the tubing but provides a more controlled NO release from the donor as well. This can be attributed to the silicone oil preventing the hydration on the silicone tubing, which can lead to faster release of NO from the donor.[18,18]

Assessment of fibrinogen adsorption in vitro—One common method for assessing the hemocompatibility of materials in vitro is to examine the ability of the material to resist protein adhesion, more specifically, fibrinogen. The conversion of fibrinogen to fibrin in the common pathway of the coagulation cascade, and the adhesion of platelets through GpIIb/IIIa, lead to the formation of thrombus on the material surface. While the orientation of fibrinogen adsorption has been shown to determine the degree of platelet adhesion, limiting protein adhesion regardless of orientation is generally considered to be an improvement in the hemocompatibility of a material.[48] Apart from aiding in the formation of thrombus, surface bound protein has been shown to increase the level of bacterial adhesion, increasing the chance of biofilm formation and infection.[30] Although NO releasing materials have been shown to significantly reduce platelet activation and adhesion, they have also been shown to adsorb higher levels of fibrinogen.[29] Therefore, developing non-fouling NO-releasing materials could provide drastic improvements in the overall hemocompatibility and antibacterial nature of these materials.

To examine if the infusion of silicone oil to provide a slippery surface could overcome the increased protein adhesion observed on NO-releasing materials, 2 hours exposure to FITC-labeled fibrinogen was conducted at 37° C. (FIG. 4). NORel-SR was observed to adsorb comparable amounts of fibrinogen compared to the control SR tubing, which coincides with previously reported results.[29] The presence of the infused oil was observed to greatly reduce protein adhesion in both LI-SR and LINORel tubing. Therefore, the infusion of silicone oil was successful in drastically reducing the adsorption of fibrinogen despite NO release. The adhesion of the protein of the surface was not measured quantitatively, although MacCullum et. al has reported that the measured bacterial adhesion on silicone oil infused tubing can vary drastically with the method that the material is washed.[33] In the present disclosure, it is shown that with no wash, ca. 90% reductions in biofilm formation was observed with LI-SR alone; however, it reduced to nearly 100% with both 5 s and 5 min wash times under high shear. The infinite dilution of this method for washing of the material surface ensures minimal shear on the material surface, and therefore represents the highest levels of protein adsorption that would be seen, with much of the protein loosely bound to the surface.

Assessment of Porcine Platelet Adhesion In Vitro

Figure 5:
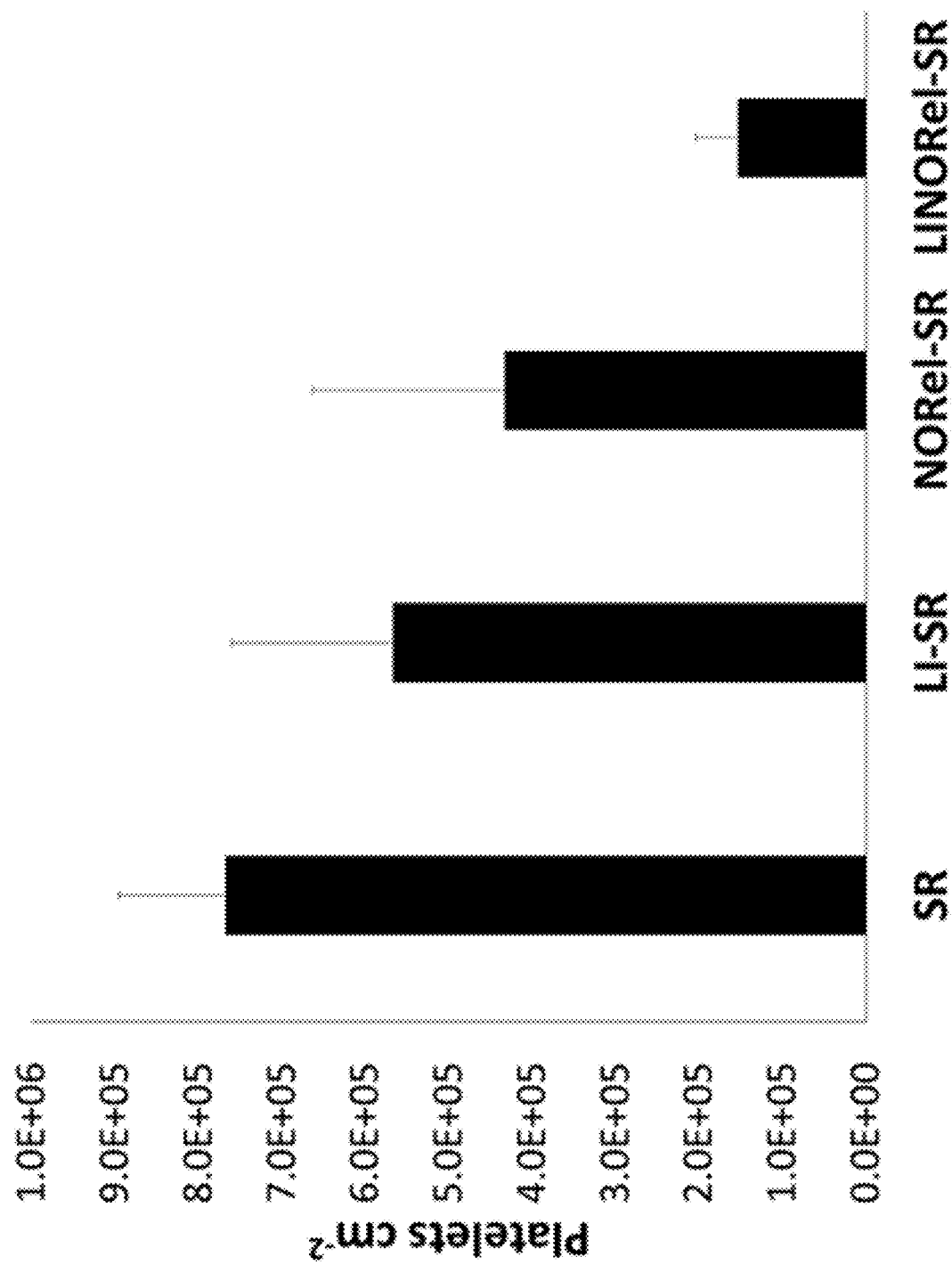
FIG. 5 provides examples of the degree of platelet adhesion on various silicone tubing after 2 hours exposure to porcine platelet rich plasma as measured using an LDH quantification assay.

Sections of the various modified Tygon™ tubing were exposed to fresh porcine PRP for 2 hours at 37° C. under mild rocking, where the number of adhered platelets were quantified using a Roche LDH assay (FIG. 5). The presence of the infused oil provides a lubricating layer, separating the material surface from the liquid to be in contact, as well as drastically reducing the surface roughness.[11,33,34] Presence of the SLIP surface resulted in 27% reduction in the overall adhered platelets ($7.76\pm1.70\times10^5$ platelets cm$^{-2}$ vs $5.67\pm2.58\ 10^5$ platelets cm$^{-2}$, p>0.05), while NORel surfaces saw reductions near 44%. Similar reductions in platelet adhesion have been reported for other liquid infused surfaces when exposed to whole blood for 30 min, containing 0.25 U mL$^{-1}$ heparin.[11] The increased platelet adhesion observed in the present disclosure can be attributed to the increased exposure time and absence of anticoagulant. The combination of infused oil with a NO releasing donor molecule further reduced the degree of platelets adhered to $81.7\pm2.5\%$ of control silicone rubber tubing ($7.76\pm1.70\times10^5$ platelets cm$^{-2}$ vs $1.52\pm0.68\times10^5$ platelets cm$^{-2}$, p=0.03). The LINORel combination was able to significantly reduce platelet adhesion when compared to LI-SR alone (73.1%, p=0.03), and may be attributed to the presence of the silicone oil as it does not prevent platelet activation. However, the LINORel combination did not provide a significant decrease in platelet adhesion when compared to NORel-SR alone (p>0.05). Washing of each material was done through infinite dilution of the well plate, and therefore provided minimal shear at the material interface. The effectiveness of the washing of these liquid infused materials is highly depended on the shear rate and time of wash, and can attribute to higher platelet counts observed.[33] Few dual-action materials incorporating NO release have been developed, with even fewer examined for platelet adhesion in vitro. Kipper et. al, developed a glycoclyx-inspired NO releasing material on titanium to mimic the natural endothelium, where NO release was provided by nitrosated chitosan thioglycolic acid.[49] These materials showed similar reductions in platelet adhesion to the LINORel tubing when examined using scanning electron microscopy after 2 hours exposure to human blood plasma containing platelets and leukocytes. However, the NO release from the materials decreased to below $0.01\times10^{-10}$ mol min$^{-1}$ cm$^{-2}$ within 20 minutes. The combination of NO with zwitterionic polycarboxybetaine coatings have been reported by Cook et. al with similar platelet adhesion to the LINORel materials describe with $93.1\pm1.3\%$ reductions in platelet adhesion using NO delivery through a permeable polydimethylsiloxane membrane. While this combination is highly effective, the requirement for sweep gas may limit the direct application. Therefore, the combination of the extended non-fouling nature from the SLIP surface with controlling of the NO release profile make the LINORel approach a promising for long term blood-contacting applications.

In Vitro 7 Day Bacterial Adhesion and Viability Analysis in a Continuous Flow CDC Bioreactor Development of novel materials to reduce bacterial adhesion and growth on materials are generally achieved using one of or a combination of two parameters: (i) the surface characteristics of the material (chemical and physical), and (ii) the antibacterial efficiency attributed to it via the antimicrobial agent. The LINORel approach looks to address each of these parameters by combing an active release of and antibacterial agent (NO) with a liquid-infused surface. While the infused silicone oil provides a super slippery hydrophobic surface for preventing attachment of bacteria on the polymer surface in an environment with shear force (such as CDC bioreactor), the free radical NO provides bactericidal action via lipid oxidation, denaturation of enzymes, and deamination of DNA.[50] To examine the long-term efficacy of these materials to prevent biofilm formation, exposure to two common pathogens associated with healthcare-acquired infections was done in a CDC bioreactor over a 7 day period with gram-negative *P. aeruginosa* and gram positive *S. aureus*, where *P. aeruginosa* causes 10-15% of nosocomial infections worldwide.[33,51].

Figure 6A:
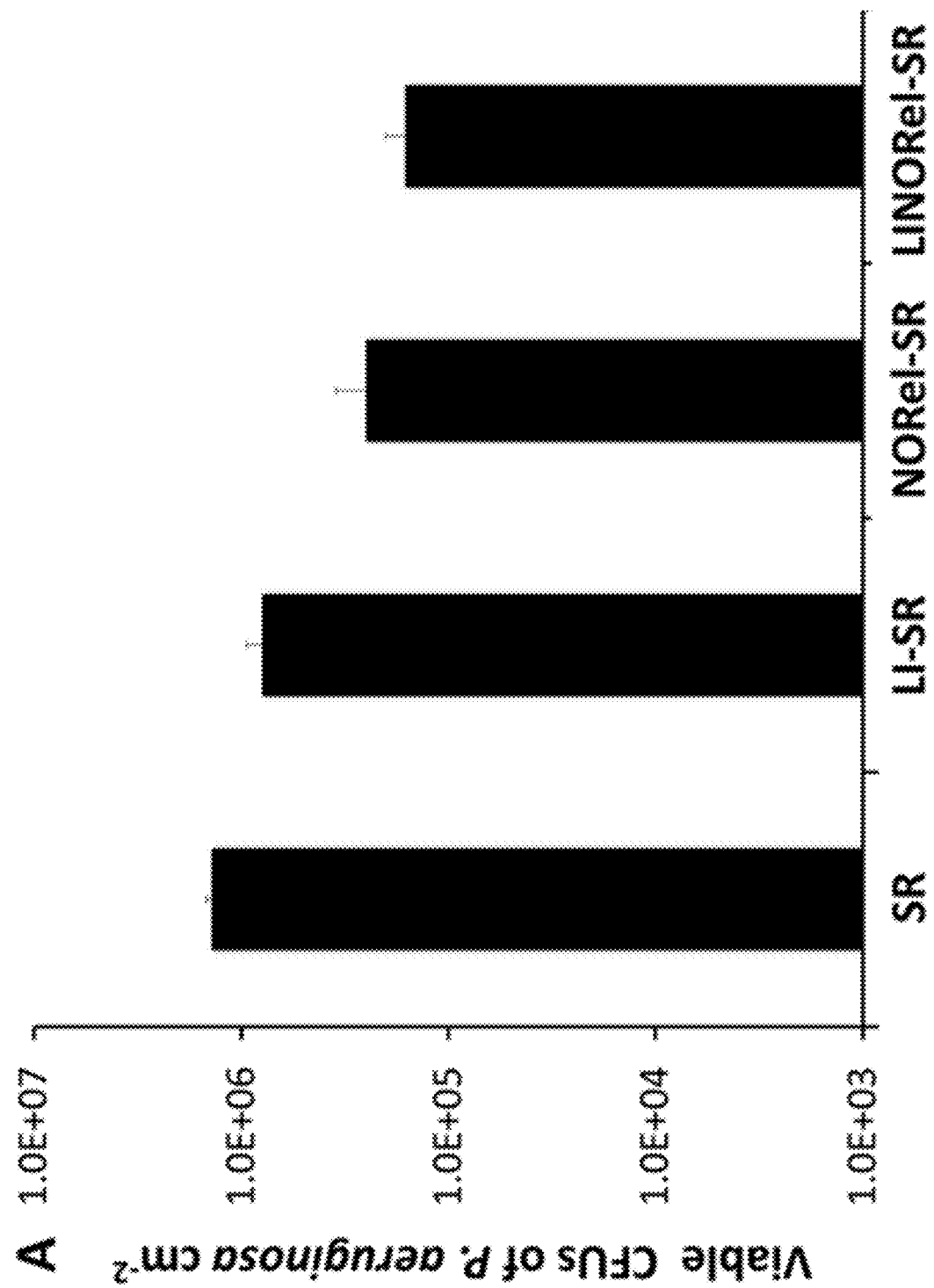
FIGS. 6A-B show counts of viable bacteria on various silicone tubing after 7 days of bacteria exposure in a CDC bioreactor.
Figure 6B:
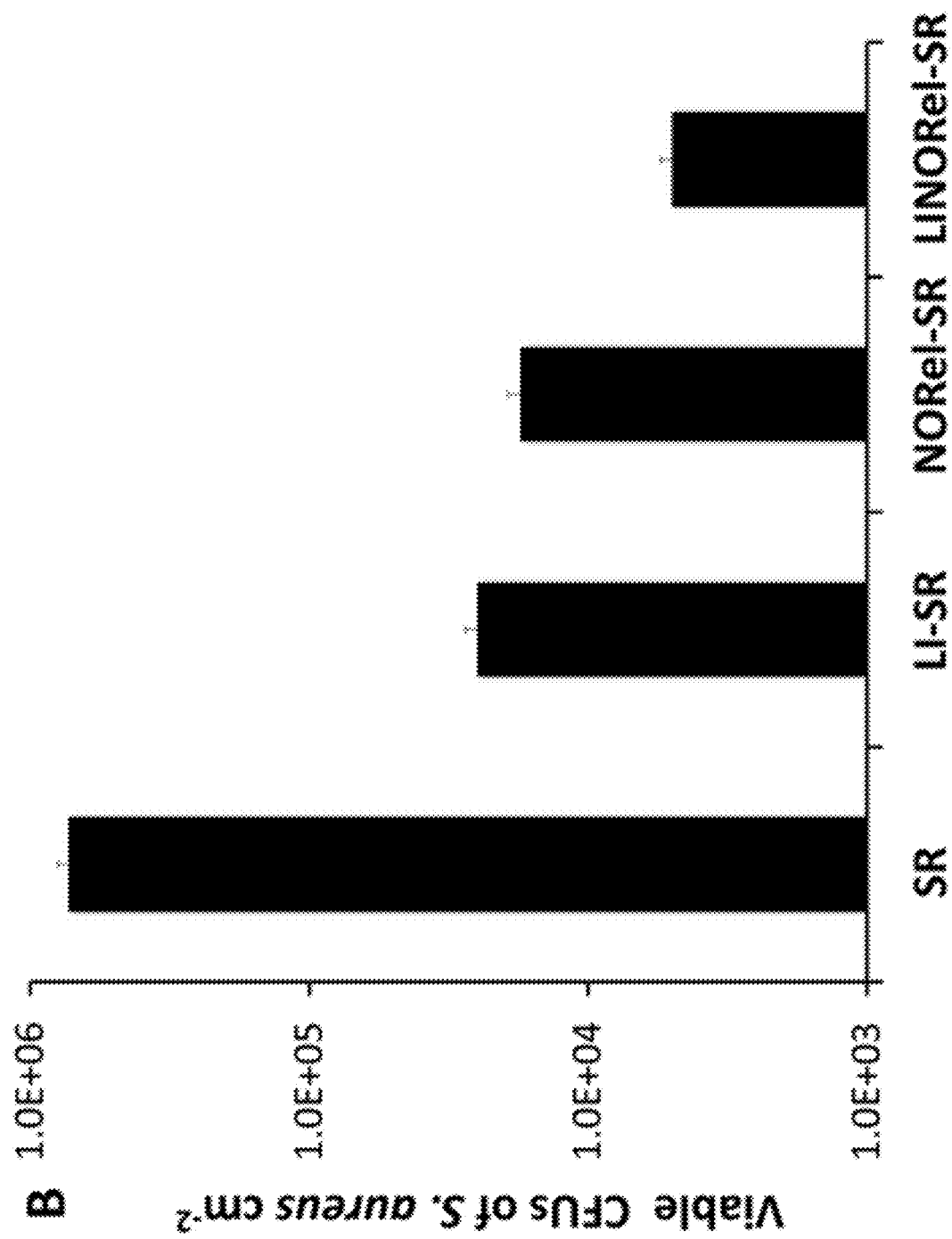

In a similar fashion to the protein adhesion studies mentioned above, minimal washing of the surface was done as to not detach loosely bound bacteria from the material surface through shear forces prior to the intentional detachment via homogenization of the film. FIG. 6 graphically represents the CFU cm$^{-2}$ attached on the surface of each of modified tubing. Efficacy of each tubing modification is summarized in Table 1.

the ability of the liquid infused surface to reduce bacterial adhesion and NO to provide bactericidal activity can vary between bacterial strains, and should be investigated further with the bacterial strain that will apply to the intended device. The NO based strategy to prevent infection is not expected to stimulate resistance in the bacterial strains due to its rapid mode of action and very short half-life (<5 sec) unlike antibiotics and silver nanoparticles.[22,64] Further developing these materials to release levels of NO at the upper end of physiological limits would be expected to provide further reductions in long-term viable bacterial adhesion. LINORel-SR achieved a 99.3±1.9% reduction in gram-positive *S. aureus* and 88.5±3.3% reduction in *P. aeruginosa* population on LINORel tubing (CFU mL$^{-1}$) as compared to control SR tubing, and was significantly more effecitvive than LI-SR or NORel-SR tubing alone (Table 2). The effect of the LINORel combination is clearly demonstrated, where reductions of the combination are near the reductions observed when comparing a singular modification to the unmodified SR.

TABLE 1

Efficacy of each modification of SR on reducing bacterial adhesion and viability over 7 days in CDC bioreactor.

| | S. aureus | | | | P. aeruginosa | | | |
|---|---|---|---|---|---|---|---|---|
| | SR | LI-SR | NORel-SR | LINORel-SR | SR | LI-SR | NORel-SR | LINORel-SR |
| CFU × 10$^5$ cm$^{-2}$ | 7.29 ± 1.11 | 0.25 ± 0.02 | 0.17 ± 0.04 | 0.05 ± 0.01 | 13.92 ± 1.22 | 7.95 ± 0.53 | 2.49 ± 0.02 | 1.61 ± 0.14 |
| Reduction vs. SR (%) | — | 96.57 ± 0.3 | 97.61 ± 0.62 | 99.31 ± .15 | — | 42.89 ± 3.80 | 82.08 ± 0.18 | 88.44 ± 1.01 |
| p value vs. SR | — | 0.007 | 0.008 | 0.007 | — | 0.004 | 0.002 | 0.003 |

The presence of the infused silicone oil alone reduced CFU cm$^{-2}$ of *S. aureus* by 96.5±0.30% and *P. aeruginosa* by 42.8±3.8% after 7 days in the CDC environment. The drastic difference in the ability for LI-SR to prevent the attachment of *P. aeruginosa* can be attributed to the differences in the structure of the bacteria, and demonstrate the need for an active release of a bactericidal agent such as NO when used in long-term applications. Previously, infusion of silicone oil was shown to reduce *P. aeruginosa* adhesion to medical grade silicone by >90% after 48 hours exposure.[33] Many of the interactions of bacteria with liquid infused materials are not fully understood. This increase in *P. aeruginosa* adhesion at day 7 could stem from the proliferation of few bacteria that had adhered, or overcoming the liquid layer with extended exposure. NORel-SR achieved 97.6±0.6% and 82.1±0.2% reductions against *S. aureus* and *P. aeruginosa* respectively. The NO flux of the tubing dropped from 0.62±0.09×10$^{-10}$ mol min$^{-1}$ cm$^{-2}$ to 0.09±0.07×10$^{-10}$ mol min$^{-1}$ cm$^{-2}$ from the initial release to day 7, therefore it would not be unreasonable to predict that the bacterial killing was much higher initially, decreasing over time due to gradual decrease in NO flux. The bacterial killing ability of the NO releasing tubing matches with the previous reports where the bactericidal activity of NO has been demonstrated against *S. aureus*, *E. coli*, *Candida albicans*, *L. monocytogenes*, *E. faecalis* and *A. baumanni*.[22,41,52,53] However, both

TABLE 2

Comparison of LINORel-SR tubing to LI-SR and NORel-SR after 7 days in CDC bioreactor.

| | S. aureus | | P. aeruginosa | |
|---|---|---|---|---|
| | LI-SR vs. LINORel | NORel-SR vs. LINORel | LI-SR vs. LINORel | NORel-SR vs. LINORel |
| Reduction vs. LINORel (%) | 80.0 ± 4.7 | 71.3 ± 4.9 | 73.2 ± 2.2 | 35.5 ± 5.7 |
| p value vs LINORel | 0.001 | 0.044 | 0.003 | 0.004 |

Integration of biocides into materials to provide antibacterial activity to SLIPs surfaces have been reported by using the combination of triclosan with infused silicone oil in polyethyleneimine/poly(2-vinyl-4,4-dimethylazlactone) (PEI/PVDMA) multilayers, and showed ca. 80% reduction in *C. albicans* after three sequential 24 hour exposures to 1 mL cell suspension (10$^6$ CFU/mL).[37] However, the biomimetic nature of NO releasing materials is attractive with the emergence of antibiotic-resistant strains of bacteria, as well having antithrombotic properties. Dual action mechanisms to increase the bactericidal activity of NO releasing materials using the combination of NO release with metallic ions[46,55], quaternary ammonium compounds[56,57], antibiotics and antimicrobial peptides[58] have also been investigated. While the combination of bactericidal agents may provide higher bactericidal activity in the short-term, these materials can experience decreases in efficacy with fouling of the material surface. Therefore, adding bactericidal activity to SLIP materials can be advantageous in protein-rich or bacterial-rich environments where the surface can be compromised quickly.

Cytocompatibility of LINORel-SR Tubing

Figure 7:
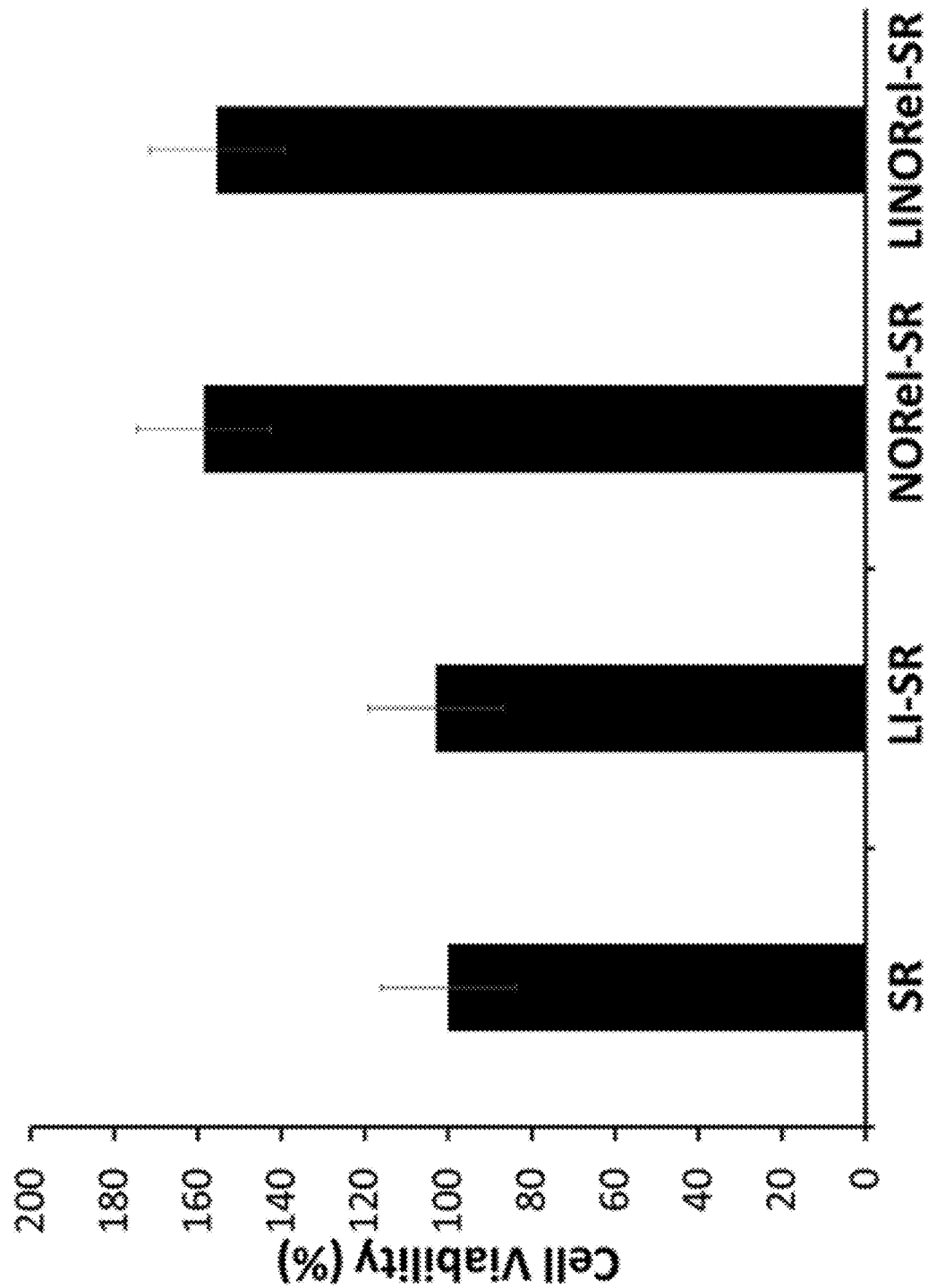
FIG. 7 illustrates cytocompatibility and cell growth support of various infused SR tubing towards mouse fibroblast cells in 24 hour study.

The CCK-8 assay was performed to demonstrate the absence of any toxic response of the leachates from NORel-SR and LI-SR tubing towards mouse fibroblast cells. The results demonstrated that neither NORel nor LI-SR, nor their combination in the used dosages, is cytotoxic to the mammalian fibroblast cells. In the past SNAP and Si-oil has been used individually as an active strategy to control the growth of bacteria on the polymeric surface, however, this would be the first report to show that the leachates from the applied concentration of SNAP and Si-Oil intergrated in the tubing is not cytotoxic to the mammalian cells but still very effective in terms of bacterial inhibition and preventing platelet adhesion The results demonstrated that not only the leachates not caused any cytotoxic response but at the same time also promoted the proliferation of the mouse fibroblast cells. This can be mainly due to the cell proliferating potential of NO that would have released as a result of putting the tubes in contact with cell culture media. FIG. 7 shows the cell proliferation capacity of NO-releasing silicone tubes. It was previously shown that SNAP incorporation in the medical grade polymer resulted in no cytotoxicity in a 24 hour study in vitro.[44,46] This is in line with the recent studies which demonstrated endogenous NO has to be important in mammalian cell proliferation. Ziche et al., reported that NO induces endogenous basic fibroblast growth factor (bFGF) resulting in upregulation of urokinase-type plasminogen activator (uPA) in coronary venular endothelial cells (CVECs) ultimately resulting in the proliferation of endothelial cells.[59] Another study has shown similar results where endogenous NO was shown to cause an increase in proliferation of endothelial cells from postcapillary venules by promoting DNA synthesis in these cells.[60] However, the present disclosure demonstrated the cell proliferation via NO release from the leachate solution as a result of soaking tubing samples in DMEM medium for 24 hours.

In the present disclosure, the combination of liquid-infused slippery surfaces was combined with NO-releasing capabilities in commercial medical grade silicone rubber tubing through the infusion of silicone oil and the NO donor SNAP. The presence of SNAP in the silicone matrix had no significant negative effects on the slippery nature of the surface, with no significant changes in the swelling ratio or sliding angle over 7 days. However, the infusion of silicone oil assisted in the controlled release of NO due to limiting the hydration of the SR. Silicone tubing infused with SNAP showed a decrease in NO-release from $0.62\pm0.09\times10^{-10}$ mol min$^{-1}$ cm$^{-2}$ to $0.09\pm0.07\times10^{-10}$ mol min$^{-1}$ cm$^{-2}$ over the 7 day period, while the LINOrel-SR tubing showed a much more constant release of $0.35\pm0.03\times10^{-10}$ mol min$^{-1}$ cm$^{-2}$ and $0.42\pm0.06\times10^{-10}$ mol min$^d$ cm$^{-2}$. The infusion of silicone oil reduced fibrinogen adsorption over a 2 hour period for both LI-SR and LINORel-SR tubing. Bacterial adhesion was investigated over a 7 day period using a CDC bioreactor, where 99.3±1.9% and 88.3±3.3% reductions in viable cell adhesion were observed for S. aureus and P. aureginosa, respectively. The combination of SNAP and silicone oil was confirmed to be non-cytotoxic towards mammalian fibroblast cells Instead it resulted in the proliferation of mammalian cells due to the possible presence of NO in the leachouts. Overall, the results suggested that the infusion of SNAP and silicone oil into commercial silicone tubing can potentially increase the biocompatibility for medical applications while preventing infection.

Experimental Section

All methods were performed in accordance to the University Committee on the Use and Care of Animals, and with university and federal regulations.

Materials

N-Acetyl-D-penicillamine (NAP), sodium chloride, copper chloride, L-cysteine, potassium chloride, sodium phosphate dibasic, potassium phosphate monobasic, ethylenediaminetetraacetic acid (EDTA), tetrahydrofuran (THF), and sulfuric acid were purchased from Sigma-Aldrich (St. Louis, MO). Methanol, hydrochloric acid, silicone oil, and sulfuric acid were obtained from Fisher Scientific (Pittsburgh, PA). Saint-Gobain™ Tygon™ Formula 3350 silicone rubber (SR) tubing was purchased from Fisher Scientific (Pittsburgh, PA). All aqueous solutions were prepared with 18.2 MΩ deionized water using a Milli-Q filter (Millipore Corp., Billerica, MA). Phosphate buffered saline (PBS), pH 7.4, containing 138 mM NaCl, 2.7 mM KCl, 10 mM sodium phosphate, 100 µM EDTA was used for all in vitro experiments. Trypsin-EDTA and Dulbecco's modification of Eagle's medium (DMEM) were obtained from Corning (Manassas, VA 20109). The antibiotic Penicillin-Streptomycin (Pen-Strep) and fetal bovine serum (FBS) were purchased from Gibco-Life Technologies (Grand Island NY 14072). The Cell Counting Kit-8 (CCK-8) was obtained from Sigma-Aldrich (St Louis MO 63103). The bacterial strains of Pseudomonas aeruginosa (ATCC 27853), Staphylococcus aureus (ATCC 6538) and 3T3 mouse fibroblast cell line (ATCC 1658) were originally obtained from American Type Culture Collection (ATCC).

SNAP Synthesis Protocol

SNAP was synthesized using a modified version of a previously reported method.[61] Briefly, an equimolar ratio of NAP and sodium nitrite was dissolved in a 1:1 mixture of water and methanol containing 2 M HCl and 2 M $H_2SO_4$. After stirring, the reaction vessel was cooled in an ice bath to precipitate the green SNAP crystals. The crystals were collected by filtration, rinsed with water, and dried under ambient conditions. The reaction mixture and resulting crystals were protected from light at all times.

Preparation of NORel and LINORel Tubing

The SNAP swelling solution was prepared by dissolving SNAP in THF using a concentration of 25 mg mL$^{-1}$ as found previously to provide an optimized NO-release.[27] The Saint-Gobain™ Tygon™ SR tubing was soaked in the SNAP swelling solution for 24 h. The tubing was removed, briefly rinsed with PBS, and dried for 48 hours under ambient conditions to allow the excess THF to evaporate. After drying, the tubing samples were placed in a 20 mL vial with DI $H_2O$, and placed in a Fisher Scientific 1.9 L sonicating bath for 5 min to remove any crystalized SNAP from the surface of the tubing. The tubing and swelling solutions were protected from light throughout the swelling process. Infusion of silicone oil for LINORel tubing was then acheived through incbuation of NORel SR tubing in silicone oil for 72 hours at room temperature, and protected from light.

Nitric Oxide Release and Total SNAP Loading

Nitric oxide release from the silicone tubing was measured using a Sievers chemiluminescence Nitric Oxide Analyzer (NOA), model 280i (Boulder, CO). A section of the NORel-SR or LINOREl-SR tubing (1 cm) was placed in 4 mL PBS with EDTA buffer at 37° C. Nitric oxide purged from the submerging buffer through bubbled nitrogen and was continuously swept from the headspace of the sample cell with a nitrogen sweep gas to the chemiluminescence detection chamber. The nitrogen flow rate was set to 200 mL/min with a chamber pressure of 6 Torr and an oxygen pressure of 6.0 psi. The NO-release from samples is normalized by the surface area using the flux unit ($x10^{-10}$ mol $cm^{-2}$ $min^{-1}$). Both NORel-SR and LINORel-SR samples were incubated at 37° C. in 4 mL PBS with EDTA between NO release measurements to maintain physiological conditions. The buffer was changed daily as to ensure the buffer was not saturated with either SNAP nor silicone oil.

Total loading of SNAP using the swelling process was measured by incubating a small section of the NORel-SR tubing (10-20 mg) in a solution of 50 mM $CuCl_2$ and 10 mM L-cysteine at 37° C.[28] The addition of L-cysteine aids in the catalysis of $Cu^{2+}$ to $Cu^+$, which is responsible for the catalytic release of NO from RSNOs such as SNAP.[62] Release rates of NO were then integrated over the duration of the measurement to determine the total NO released.

Oil Swelling

Swelling and deswelling characteristics of the silicone tubing were investigated. For swelling, silicone tubing and NORel-SR were submerged in silicone oil (Alfa Asar). The mass swelling ratio can be defined as the ratio of the mass of the infused polymer ($M_i$) and the mass of the polymer initially (Mo) (equation 1).

$$\text{Swelling ratio} = \frac{M_i}{M_0} \quad (1)$$

Deswelling of the oil from the respective tubing was examined through incubation of the swollen tubing in PBS with EDTA at 37° C. under mild agitation on a Medicus rocker.

Sliding Angle Characterization

A sliding stage with a digital protractor was used to measure the sliding angle of a 10 µL droplet of water on the surface of each silicone substrate. Tubing samples (ca. 5 cm in length) were cut longitudinally and mounted onto a glass slide to create a flat sheet of silicone. Samples were gently washed with DI $H_2O$ and air-dried with nitrogen to remove any dust or contaminants that were initially on the surface. For each measurement, the angle of the sample was slowly increased until the droplet was observed to slide along the surface, and the angle was recorded using a digital protractor. Each surface was measured at 6 different randomly selected areas. Samples were stored in 50 mL conical tubes containing 40 mL of PBS with EDTA, and maintained at 37° C. in a Thermo Fisher water jacketed incubator, under mild agitation on a Medicus blood rocker. The buffer was replaced after each measurement to avoid saturation of the oil in the incubating buffer. Samples were gently blown dry with nitrogen after being removed from the incubating buffer to ensure any water on the surface did not interfere with the sliding angle measurement.

Leaching of SNAP from NORel-SR and LINORel-SR Tubing

Total leaching of SNAP during the oil swelling and first 24 hours of use were examined at physiological conditions. Nitric oxide releasing tubing was fabricated as described in the Preparation of SNAP Impregnated Tubing section. Phosphate buffered saline (PBS) with 100 mM EDTA was adjusted to a pH of 7.4 was used, where EDTA was used to ensure any metal ions in the PBS solution are neutralized as metallic ions can act as a catalyst for the decomposition of SNAP to release NO. The NO releasing tubing was submerged in 4 mL of PBS-EDTA, and allowed to incubate at 37° C. in a Thermo Fisher water jacketed incubator and was protected from light. At each time point, the concentration of SNAP in the PBS-EDTA buffer was measured using a Thermo Scientific Genysis 10S UV-Vis Spectrophotometer and reintroduced to the sample container as to not alter the total incubation volume throughout the measurement period. The SNAP molecule has maxima at 340 and 590 nm, corresponding to the S—NO bond.[18,47,63] Absorbance was recorded for each sample, and concentration was determined using a predetermined calibration curve for known concentrations of SNAP in the PBS/EDTA solution. The pure PBS/EDTA solution was used as a blank for all measurements.

Leaching of SNAP from the silicone tubing was repeated during the oil swelling process as well, to ensure large amounts of SNAP were not lost during the 3-day swelling period. Sections of SNAP impregnated tubing were massed and placed in 4 mL of silicone oil. The absorbance spectra of silicone oil were taken to ensure no interference would be seen between the SNAP maxima and the oil. Pure silicone oil was found to have 0.0 absorbance when PBS-EDTA was used as a blank at 340 nm. Therefore, the same calibration curve of SNAP in PBS-EDTA was used for determining SNAP concentration in the silicone oil. Solubility of SNAP in silicone oil was determined by by adding 10 mg/mL and put on a vortex mixer for 2 min. The suspension was then centrifuged (10 min, 3000 rpm), and a 1 mL sample of the silicone oil was taken for UV vis spectroscopy.

Adsorption of fibrinogen in vitro—Levels of protein adhesion were quantified for the fabricated materials using a modified version of a previously reported method.[48] FITC labeled human fibrinogen (13 mg/mL, Molecular Innovations) was diluted to achieve 2 mg $mL^{-1}$ in phosphate buffer solution (pH 7.4). Sections of the various SR tubing were incubated at 37° C. for 30 minutes in a 96 well plate, followed by the addition of the stock protein solution to achieve a concentration of 2 mg $mL^{-1}$.[48] During the addition of the stock solution, the tip of the pipette was held below the air-water interface to avoid denaturing of the protein. Following 2 hours of incubation, infinite dilution of the wells' contents was carried out to wash away the bulk and any loosely bound protein from the materials. Samples were then imaged under an EVOS FL fluorescent microscope to qualitatively assess the degree of protein adhesion on the surface. All images were taken at an equal light intensity.

Assessment of platelet adhesion in vitro—All protocols pertaining to the use of whole blood and platelets were approved by the Institutional Animal Care and Use Committee. Freshly drawn porcine blood was drawn into a BD 60 mL syringe with 3.4% sodium citrate at a ratio of 9:1 (blood:citrate) through a blind draw.

Immediately following the draw, the anticoagulated blood was centrifuged at 1100 rpm for 12 min using the Eppendorf Centrifuge 5702. The platelet rich plasma (PRP) portion was collected carefully with a pipet as to not disturb the buffy coat. The remaining samples were then spun again at 4000 rpm for 20 min to achieve platelet poor plasma (PPP). Total platelet count in both the PRP and PPP fractions were determined using a hemocytometer (Fisher). The PRP and PPP were combined in a ratio to give a final platelet concentration ca. $2\times10^8$ platelets $mL^{-1}$. Calcium chloride ($CaCl_2$) was added to the final platelet solution to achieve a final concentration of 2.5 mM.[48]

Sections of each respective tubing were cut into small sections (0.5 cm long) and placed in a 48 well plate. Approximately 1.5 mL of the calcified PRP was added to each well containing a catheter sample, with one sample per well, and incubated at 37° C. for 90 min with mild rocking (25 rpm) on a Medicus Health blood tube rocker. Following the incubation, the wells were infinitely diluted with 0.9% saline.

The degree of platelet adhesion was determined using the lactate dehydrogenase (LDH) released when the adherent platelets were lysed with a Triton-PBS buffer (2% v/v Triton-X-100 in PBS) using a Roche Cytotoxicity Detection Kit (LDH). A calibration curve was constructed using known dilutions of the final PRP, and the platelet adhesion on the various tubing samples was determined from the calibration curve.

In vitro bacterial adhesion and growth in a continuous flow CDC bioreactor—The ability of the LINORel-SR tubing to prevent bacterial binding and growth on the polymeric surface was tested in vitro in a continuous flow CDC bioreactor against gram-positive (*Staphylococcus aureus*) and gram negative (*Pseudomonas aeruginosa*). The use of CDC bioreactor provides a highly favorable environment for bacterial growth and biofilm formation through a continuous supply of nutrients so that antimicrobial efficacy of LINORel-SR tubing can be tested for a prolonged time interval. In the present disclosure, the long-term performance of the SNAP-Si oil and control (without SNAP and/or Si-oil coat) tubing was examined in a 7-day model. A single isolated colony of the bacterial strains was incubated overnight in LB medium for 14 hours at 150 rpm at 37° C. The optical density (O.D) was measured at 600 nm (OD600) using UV-vis spectrophotometer. All samples (SR, LI-SR, NORel-SR, and LINORel-SR; N=3 each) were sterilized with UV irradiation under a Biosafety Cabinet (BSC) and fitted inside the CDC bioreactor. The CDC bioreactor was sterilized using high pressure saturated steam for 30 min at 121° C. in an autoclave. The CDC bioreactor (working volume 1000 mL) with 400 mL of LB medium (2 g L$^{-1}$) was inoculated with the bacterial culture in a manner that the final OD600 falls in the range of $10^7$-$10^9$ CFU mL$^{-1}$ to simulate the chronic infection conditions. The CDC bioreactor on one end was connected to a feed bottle having a continuous supply of sterile LB medium (2 g L$^{-1}$) and to a sealed container to collect the wash out in a sterile manner on the other end. After 7 days, samples were removed under a BSC and gently rinsed with PBS, pH 7.4 in order to remove any loosely bound bacteria. The rinsed films were then transferred to a 15 mL tube with 2 mL sterile PBS and homogenized for 60 sec using an OmniTip homogenizer.[23] The shear force from the homogenizer tip ensured the transfer of the bound bacterial strains from the tubing to the PBS solution. Thereafter, serial dilution ($10^{-1}$ to $10^{-5}$) were made suing sterile PBS and bacterial strains were plated on Petri-dishes solid LB-agar medium using an L-spreader. The antimicrobial efficacy of the LINOrel-SR tubing was measured relative to the SR control rubing using equation 2.

$$\% \text{ Bacterial inhibition} = \frac{\left(\frac{CFU}{cm^2} \text{ in control} - \frac{CFU}{cm^2} \text{ in test}\right) \times 100}{\frac{CFU}{cm^2} \text{ in control}} \quad (2)$$

In vitro cytocompatibility—The ability of the NORLI-SR tubing to generate any cytotoxic responses was tested on mouse fibroblast cells (ATCC-1658) using cell counting kit-8 (CCK-8) assay in accordance with ISO 10993 standard. The CCK-8 assay is based on the reduction of highly water-soluble tetrazolium salt. WST-8 [2-(2-methoxy-4-nitrophenyl)-3-(4-nitrophenyl)-5-(2,4-disulfophenyl)-2H-tetrazolium monosodium salt] by dehydrogenases present in viable mammalian cells to give formazan (an orange color product) in direct proportion to the number of viable cells when detected at a wavelength 450 nm. Mouse fibroblast cells were cultured in a humidified atmosphere with 5% CO2 at 37° C. in 75 cm$^2$ T-flask containing premade DMEM medium (Thermo Fischer) with 10% fetal bovine serum (FBS) and 1% penicillin-streptomycin. After the confluency reached 80%-90%, cells were removed from the flask using 0.18% trypsin and 5 mM EDTA, counted using bromphenol blue in a hemocytometer and 100 µL of 5000 cells mL$^{-1}$ were seeded in 96 well plates. The leachates from the each sample (control SR, NORel-SR, LI-SR and LINORel-SR) was obtained by soaking 10 mg of tubing sample in 10 mL DM EM medium for 24 hours at 37° C. in the amber vial (N=5 each). To each of the wells containing fibroblast cells, 10 µL of the CCK-8 solution was added and cells with CCK-8 dye were incubated for 3 h. Negative controls containing 5000 cells/ml were grown in 5 separate wells for reference to compare with the cells treated with leachates. Absorbance values were measured at 450 nm and the relative cell viability of mammalian cells exposed to the respective leachates were compared. 100 µL of the DM EM medium without cells was added in 5 of the wells and used as blank to adjust the background interference from DMEM media. Results were reported as percentage cell viability difference between the leachate treated cells relative to the negative control (without leachate treatment) using equation 3.

$$\% \text{ Cell Viability} = \frac{\text{Absorbance of the test samples}}{\text{Absorbance of the control samples}} \times 100 \quad (3)$$

Statistical Analysis

Data is reported as the mean±standard deviation. Statistical significance was determined using a two-tailed t-test assuming unequal variances with α=0.05. All measurements were conducted with N=3 samples unless otherwise stated.

Example 2

Commercial silicone Foley catheters can be successfully impregnated with a nitric oxide (NO) donor and silicone oil to create a liquid-infused nitric oxide releasing urinary catheter using a two stage swelling method. The NO donor used is S-nitroso-N-acetylpenicillamine (SNAP). The catheters were swelled with a swelling solution containing 125 mg mL$^{-1}$ concentration of SNAP in tetrahydrofuran (THF) for a 24-hour period. After the incorporation of SNAP, the modified urinary catheter was then submerged in silicone oil to swell for a 72-hour period, allowing ample time for the silicone oil to infiltrate the polymer matrix and create a slippery surface. The NO release measurements were tested using a Sievers chemiluminescence Nitric Oxide Analyzer. The sole impregnation of SNAP to create a nitric oxide releasing urinary catheter (NORel-UC) resulted in a NO release at a level between $1.62\pm0.59\times10^{-10}$ mol cm$^{-2}$ min$^{-1}$ and $0.35\pm0.05\times10^{-10}$ mol cm$^{-2}$ min$^{-1}$ over a 60-day period. While the combination of both SNAP and silicone oil to create a liquid-infused nitric oxide releasing urinary catheter (LINORel-UC) sustained a controlled NO release at a level between $0.4\pm0.04\times10^{-10}$ mol cm$^{-2}$ min$^{-1}$ and $0.84\pm0.18\times10^{-10}$ mol cm$^{-2}$ min$^{-1}$ for a 60-day period. The presence of silicone oil decreases the large initial burst of NO early in the testing period, typical of NO releasing materials, and prolongs the NO release at a steadier level over the 60-day period.

REFERENCES

1. Brisbois, E. J., Handa, H. & Meyerhoff, M. E. in *Advanced Polymers in Medicine* 481-511 (Springer, 2015).
2. Vertes, A., Hitchins, V. & Phillips, K. S. Analytical challenges of microbial biofilms on medical devices. *Analytical chemistry* 84, 3858-3866 (2012).
3. O'Grady, N. P. et al. Guidelines for the prevention of intravascular catheter-related infections. *Clinical infectious diseases* 35, 1281-1307 (2002).
4. Paden, M. L., Conrad, S. A., Rycus, P. T. & Thiagarajan, R. R. Extracorporeal life support organization registry report 2012. *ASAIO journal* 59, 202-210 (2013).
5. Smith, R. S. et al. Vascular catheters with a nonleaching poly-sulfobetaine surface modification reduce thrombus formation and microbial attachment. *Science translational medicine* 4, 153ra132-153ra132 (2012).
6. Zheng, S., Yang, Q. & Mi, B. Novel antifouling surface with improved hemocompatibility by immobilization of polyzwitterions onto silicon via click chemistry. *Applied Surface Science* 363, 619-626 (2016).
7. Kovach, K. et al. In vitro evaluation and in vivo demonstration of a biomimetic, hemocompatible, microfluidic artificial lung. *Lab on a Chip* (2015).
8. Kovach, K. M., Capadona, J. R., Sen Gupta, A. & Potkay, J. A. The effects of PEG-based surface modification of PDMS microchannels on long-term hemocompatibility. *Journal of Biomedical Materials Research* Part A (2014).
9. Peppas, N. A. & Langer, R. New challenges in biomaterials. *Science* 263, 1715-1720 (1994).
10. Larm, O., Larsson, R. & Olsson, P. A new non-thrombogenic surface prepared by selective covalent binding of heparin via a modified reducing terminal residue. *Biomaterials, medical devices, and artificial organs* 11, 161-173 (1983).
11. Leslie, D. C. et al. A bioinspired omniphobic surface coating on medical devices prevents thrombosis and biofouling. *Nature biotechnology* 32, 1134-1140 (2014).
12. Cronin, R. E. & Reilly, R. F. in *Seminars in dialysis*. 510-515 (Wiley Online Library).
13. Annich, G. Extracorporeal life support: the precarious balance of hemostasis. *Journal of Thrombosis and Haemostasis* 13 (2015).
14. Shepherd, G., Mohorn, P., Yacoub, K. & May, D. W. Adverse drug reaction deaths reported in United States vital statistics, 1999-2006. *Annals of Pharmacotherapy* 46, 169-175 (2012).
15. Chen, Y.-M. et al. Effectiveness of silver-impregnated central venous catheters for preventing catheter-related blood stream infections: a meta-analysis. *International Journal of Infectious Diseases* 29, 279-286 (2014).
16. Pant, J., Goudie, M., Brisbois, E. & Handa, H. in *Advances in Polyurethane Biomaterials* 471-550 (Elsevier, 2016).
17. Hou, Y., Janczuk, A. & Wang, P. Current trends in the development of nitric oxide donors. *Current Pharmaceutical Design* 5, 417-442 (1999).
18. Brisbois, E. J., Handa, H., Major, T. C., Bartlett, R. H. & Meyerhoff, M. E. Long-term nitric oxide release and elevated temperature stability with S-nitroso-N-acetylpenicillamine (SNAP)-doped Elast-eon E2As polymer. *Biomaterials* 34, 6957-6966 (2013).
19. Joslin, J. M., Lantvit, S. M. & Reynolds, M. M. Nitric oxide releasing tygon materials: studies in donor leaching and localized nitric oxide release at a polymer-buffer interface. *ACS applied materials & interfaces* 5, 9285-9294 (2013).
20. Riccio, D. A., Coneski, P. N., Nichols, S. P., Broadnax, A. D. & Schoenfisch, M. H. Photoinitiated nitric oxide-releasing tertiary S-nitrosothiol-modified xerogels. *ACS applied materials & interfaces* 4, 796-804 (2012).
21. Reynolds, M. M. et al. Nitric oxide releasing polyurethanes with covalently linked diazeniumdiolated secondary amines. *Biomacromolecules* 7, 987-994 (2006).
22. Hetrick, E. M. & Schoenfisch, M. H. Antibacterial nitric oxide-releasing xerogels: Cell viability and parallel plate flow cell adhesion studies. *Biomaterials* 28, 1948-1956 (2007).
23. Brisbois, E. J. et al. Attenuation of thrombosis and bacterial infection using dual function nitric oxide releasing central venous catheters in a 9 day rabbit model. *Acta Biomaterialia* (2016).
24. Brisbois, E. J. et al. Reduction in thrombosis and bacterial adhesion with 7 day implantation of S-nitroso-N-acetylpenicillamine (SNAP)-doped Elast-eon E2As catheters in sheep. *Journal of Materials Chemistry B* (2015).
25. Gierke, G. E., Nielsen, M. & Frost, M. C. S-Nitroso-N-acetyl-D-penicillamine covalently linked to polydimethylsiloxane (SNAP-PDMS) for use as a controlled photoinitiated nitric oxide release polymer. *Science and Technology of Advanced Materials* 12, 055007 (2011).
26. Coneski, P. N., Rao, K. S. & Schoenfisch, M. H. Degradable Nitric Oxide-Releasing Biomaterials via Post-Polymerization Functionalization of Crosslinked Polyesters. *Biomacromolecules* 11, 3208 (2010).
27. Brisbois, E. J. et al. Improved hemocompatibility of silicone rubber extracorporeal tubing via solvent swelling-impregnation of S-nitroso-N-acetylpenicillamine (SNAP) and evaluation in rabbit thrombogenicity model. *Acta biomaterialia* 37, 111-119 (2016).
28. Colletta, A. et al. S-Nitroso-N-acetylpenicillamine (SNAP) Impregnated Silicone Foley Catheters: A Potential Biomaterial/Device To Prevent Catheter-Associated Urinary Tract Infections. *ACS biomaterials science & engineering* 1, 416-424 (2015).
29. Lantvit, S. M., Barrett, B. J. & Reynolds, M. M. Nitric oxide releasing material adsorbs more fibrinogen. *Journal of Biomedical Materials Research Part A* 101, 3201-3210 (2013).
30. Charville, G. W., Hetrick, E. M., Geer, C. B. & Schoenfisch, M. H. Reduced bacterial adhesion to fibrinogen-coated substrates via nitric oxide release. *Biomaterials* 29, 4039-4044 (2008).
31. Goudie, M. J., Brainard, B. M., Schmiedt, C. W. & Handa, H. Characterization and in vivo performance of nitric oxide—releasing extracorporeal circuits in a feline model of thrombogenicity. *Journal of Biomedical Materials Research Part A* (2016).
32. Costerton, J. W., Lewandowski, Z., Caldwell, D. E., Korber, D. R. & Lappin-Scott, H. M. Microbial biofilms. *Annual Reviews in Microbiology* 49, 711-745 (1995).

33. MacCallum, N. et al. Liquid-infused silicone as a biofouling-free medical material. *ACS Biomaterials Science & Engineering* 1, 43-51 (2014).
34. Wong, T.-S. et al. Bioinspired self-repairing slippery surfaces with pressure-stable omniphobicity. *Nature* 477, 443-447 (2011).
35. Bondurant, S., Ernster, V. & Herdman, R. (Washington, DC: National Academy Press, 1999).
36. Hartmann, R. C., Conley, C. L. & Poole, E. L. Studies on the initiation of blood coagulation. III. The clotting properties of canine platelet-free plasma. *Journal of Clinical Investigation* 31, 685 (1952).
37. Manna, U. et al. Slippery Liquid—Infused Porous Surfaces that Prevent Microbial Surface Fouling and Kill Non—Adherent Pathogens in Surrounding Media: A Controlled Release Approach. *Advanced Functional Materials* 26, 3599-3611 (2016).
38. De Groote, M. A. & Fang, F. C. NO inhibitions: antimicrobial properties of nitric oxide. *Clinical Infectious Diseases* 21, S162-S165 (1995).
39. Jones, M. L., Ganopolsky, J. G., Labbé, A., Wahl, C. & Prakash, S. Antimicrobial properties of nitric oxide and its application in antimicrobial formulations and medical devices. *Applied microbiology and biotechnology* 88, 401-407 (2010).
40. Schairer, D. O. et al. Nitric oxide nanoparticles: preclinical utility as a therapeutic for intramuscular abscesses. *Virulence* 3, 62-67 (2012).
41. Privett, B. J., Nutz, S. T. & Schoenfisch, M. H. Efficacy of surface-generated nitric oxide against *Candida albicans* adhesion and biofilm formation. *Biofouling* 26, 973-983 (2010).
42. Dijkshoorn, L., Nemec, A. & Seifert, H. An increasing threat in hospitals: multidrug-resistant Acinetobacter baumannii. *Nature Reviews Microbiology* 5, 939-951 (2007).
43. Sunenshine, R. H. et al. Multidrug-resistant *Acinetobacter* infection mortality rate and length of hospitalization. *Emerg Infect Dis* 13, 97-103 (2007).
44. Goudie, M. J. et al. Characterization of an S-nitroso-N-acetylpenicillamine-based nitric oxide releasing polymer from a translational perspective. *International Journal of Polymeric Materials and Polymeric Biomaterials* 65, 769-778, doi:10.1080/00914037.2016.1163570 (2016).
45. Wo, Y. et al. Origin of long-term storage stability and nitric oxide release behavior of CarboSil polymer doped with S-nitroso-N-acetyl-D-penicillamine. *ACS applied materials & interfaces* (2015).
46. Pant, J., Goudie, M. J., Hopkins, S. P., Brisbois, E. J. & Handa, H. Tunable nitric oxide release from S-nitroso-N-acetylpenicillamine via catalytic copper nanoparticles for biomedical applications. *ACS Applied Materials & Interfaces* (2017).
47. Frost, M. C. & Meyerhoff, M. E. Controlled photoinitiated release of nitric oxide from polymer films containing S-nitroso-N-acetyl-DL-penicillamine derivatized fumed silica filler. *Journal of the American Chemical Society* 126, 1348-1349 (2004).
48. Sivaraman, B. & Latour, R. A. The relationship between platelet adhesion on surfaces and the structure versus the amount of adsorbed fibrinogen. *Biomaterials* 31, 832-839 (2010).
49. Simon-Walker, R. et al. Glycocalyx-Inspired Nitric Oxide-Releasing Surfaces Reduce Platelet Adhesion and Activation on Titanium. *ACS Biomaterials Science & Engineering* (2016).
50. Fang, F. C. Perspectives series: host/pathogen interactions. Mechanisms of nitric oxide-related antimicrobial activity. *Journal of Clinical Investigation* 99, 2818-2825 (1997).
51. Abad, C. L. & Safdar, N. Catheter-related bloodstream infections. *Infectious Disease Special Edition* 14 (2011).
52. Brisbois, E. J. et al. Optimized polymeric film-based nitric oxide delivery inhibits bacterial growth in a mouse burn wound model. *Acta Biomater.* 10, 4136-4142, doi: http://dx.doi.org/10.1016/j.actbio.2014.06.032 (2014).
53. Sundaram, J., Pant, J., Goudie, M. J., Mani, S. & Handa, H. Antimicrobial and Physicochemical Characterization of Biodegradable, Nitric Oxide-Releasing Nanocellulose-Chitosan Packaging Membranes. *Journal of agricultural and food chemistry* (2016).
54. Feelisch, M. The use of nitric oxide donors in pharmacological studies. *Naunyn-Schmiedeberg's archives of pharmacology* 358, 113-122 (1998).
55. Deupree, S. M. et al. Synergy of nitric oxide and silver sulfadiazine against Gram-negative, -positive, and antibiotic-resistant pathogens. *Molecular pharmaceutics* 7, 2289 (2010).
56. Worley, B. V., Slomberg, D. L. & Schoenfisch, M. H. Nitric oxide-releasing quaternary ammonium-modified poly (amidoamine) dendrimers as dual action antibacterial agents. *Bioconjugate chemistry* 25, 918-927 (2014).
57. Pant, J. et al. A Multi-defense Strategy: Enhancing Bactericidal Activity of a Medical Grade Polymer with a Nitric Oxide Donor and Surface-immobilized Quaternary Ammonium Compound. *Acta Biomaterialia* (2017).
58. Ren, H., Wu, J., Colletta, A., Meyerhoff, M. E. & Xi, C. Efficient eradication of mature Pseudomonas aeruginosa biofilm via controlled delivery of nitric oxide combined with antimicrobial peptide and antibiotics. *Frontiers in Microbiology* 7 (2016).
59. Ziche, M. et al. Nitric oxide promotes proliferation and plasminogen activator production by coronary venular endothelium through endogenous bFGF. *Circulation Research* 80, 845-852 (1997).
60. Ziche, M. et al. Nitric oxide promotes DNA synthesis and cyclic GMP formation in endothelial cells from postcapillary venules. *Biochemical and biophysical research communications* 192, 1198-1203 (1993).
61. Chipinda, I. & Simoyi, R. H. Formation and stability of a nitric oxide donor: S-nitroso-N-acetylpenicillamine. *Journal of Physical Chemistry B* 110, 5052-5061, doi: 10.1021/jp0531107 (2006).
62. Dicks, A. et al. Identification of Cu+ as the effective reagent in nitric oxide formation from S-nitrosothiols (RSNO). *Journal of the Chemical Society, Perkin Transactions* 2, 481-487 (1996).
63. Shishido, S. I. M., Seabra, A. B., Loh, W. & de Oliveira, M. G. Thermal and photochemical nitric oxide release from S-nitrosothiols incorporated in Pluronic F127 gel: potential uses for local and controlled nitric oxide release. *Biomaterials* 24, 3543-3553 (2003).

It should be noted that ratios, concentrations, amounts, and other numerical data may be expressed herein in a range format. It is to be understood that such a range format is used for convenience and brevity, and thus, should be interpreted in a flexible manner to include not only the numerical values explicitly recited as the limits of the range, but also to include all the individual numerical values or sub-ranges encompassed within that range as if each numerical value and sub-range is explicitly recited. To illustrate, a concentration range of "about 0.1% to about 5%" should be interpreted to include not only the explicitly recited concentration of about 0.1 wt % to about 5 wt %, but also include individual concentrations (e.g., 1%, 2%, 3%, and 4%) and the sub-ranges (e.g., 0.5%, 1.1%, 2.2%, 3.3%, and 4.4%) within the indicated range. In an embodiment, "about 0" can refer to 0, 0.001, 0.01, or 0.1. In an embodiment, the term "about" can include traditional rounding according to significant figures of the numerical value. In addition, the phrase "about 'x' to 'y'" includes "about 'x' to about y".

It should be emphasized that the above-described embodiments of the present disclosure are merely possible examples of implementations, and are set forth only for a clear understanding of the principles of the disclosure. Many variations and modifications may be made to the above-described embodiments of the disclosure without departing substantially from the spirit and principles of the disclosure. All such modifications and variations are intended to be included herein within the scope of this disclosure.

At least the following is claimed:

1. A treated article of tubing comprising a coating on a surface of the tubing,
   wherein the coating consists of a silicone oil and a nitric oxide release agent, wherein the nitric oxide release agent has from 5 to 20 carbon atoms.

2. The treated article of tubing of claim 1, wherein the nitric oxide release agent is an S-nitroso thiol of formula O=N—S—R, wherein R is an alkyl moiety or aryl moiety.

3. The treated article of tubing of claim 1, wherein the nitric oxide release agent is selected from the group consisting of: S-nitroso-N-acetylpenicillamine, S-nitroso-glutathione, and S-nitroso-N-acetylcysteine.

4. The treated article of tubing of claim 1, wherein the nitric oxide release agent comprises about 1% to 15% by weight of the treated article of tubing.

5. The treated article of tubing of claim 1, wherein the tubing comprises an elastomer, wherein the elastomer comprises a base polymer selected from a thermoplastic polymer, a thermosetting polymer, a silicone, a polyvinyl chloride, a polyurethane, a fluoropolymer, a rubber, and a thermoplastic elastomer.

6. The treated article of tubing of claim 1, wherein the article comprises about 1% to 80% by weight of silicone oil.

7. The treated article of tubing of claim 1, wherein the article of tubing has the characteristic of being able to release nitric oxide at a rate of from about $0.01 \times 10^{-10}$ mol/min-cm$^2$ to about $4 \times 10^{-10}$ mol/min-cm$^2$, and wherein the nitric oxide release agent releases nitric oxide from an inner surface of the tubing.

8. The treated article of tubing of claim 1, wherein the nitric oxide release agent comprises an amino acid moiety.

* * * * *